United States Patent
Ladduwahetty et al.

[11] Patent Number: 5,811,431
[45] Date of Patent: Sep. 22, 1998

[54] SPIRO-SUBSTITUTED AZACYCLIC DERIVATIVES AND THEIR USE AS THERAPEUTIC AGENTS

[75] Inventors: Tamara Ladduwahetty, London; Richard Thomas Lewis, Harlow; Angus Murray MacLeod, Bishops Stortford; Kevin John Merchant, Stevenage, all of United Kingdom

[73] Assignee: Merck Sharp & Dohme Ltd., Hoddesdon, England

[21] Appl. No.: 765,360

[22] PCT Filed: Aug. 7, 1995

[86] PCT No.: PCT/GB95/01867
§ 371 Date: Jan. 7, 1997
§ 102(e) Date: Jan. 7, 1997

[87] PCT Pub. No.: WO96/05203
PCT Pub. Date: Feb. 22, 1996

[30] Foreign Application Priority Data
Aug. 8, 1994 [GB] United Kingdom ............ 9415996

[51] Int. Cl.$^6$ ................. A61K 31/445; C07D 401/04
[52] U.S. Cl. .............................. 514/278; 546/17
[58] Field of Search .......................... 546/17; 514/278

[56] References Cited
FOREIGN PATENT DOCUMENTS
9413696  6/1994  WIPO .

Primary Examiner—C. Warren Ivy
Assistant Examiner—Charanjit S. Aulakh
Attorney, Agent, or Firm—J. Eric Thies; David L. Rose

[57] ABSTRACT

The present invention relates to compounds of formula (I), wherein n is zero, 1, 2 or 3; R represents $C_{1-6}$alkyl, $C_{1-6}$alkoxy, hydroxy, halogen, cyano, trifluoromethyl $SO_2C_{1-6}$alkyl, $NR^aR^b$, $NR^aCOR^b$ or $CONR^aR^b$, where $R^a$ and $R^b$ are each H, $C_{1-4}$alkyl, phenyl or trifluoromethyl; $R^1$ represents phenyl optionally substituted by 1, 2 or 3 of $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, —$O(CH_2)_pO$— (where p is 1 or 2), halogen, cyano, nitro, trifluoromethyl, trimethylsilyl, $OR^a$, $SR^a$, $SOR^a$, $SO_2R^a$, $NR^aR^b$, $NR^aCOR^b$, $NR^aCO_2R^b$, $COR^a$, $CO_2R^a$ or $CONR^aR^b$; naphthyl; benzhydryl; or benyl, where the naphthyl group or each phenyl moiety of benzyl and benzhydryl may be substituted by $C_{1-6}$alkyl, $C_{1-6}$alkoxy, halogen or trifluoromethyl; $R^2$ represents hydogen, a substituent as defined for $R^1$ or heteroaryl selected from indazolyl, thienyl, furanyl, pyridyl, thiazolyl, tetrazolyl and quinolinyl; wherein each heteroaryl may be substituted by $C_{1-6}$alkyl, $C_{1-6}$alkoxy, halogen or trifluoromethyl; $R^3$ and $R^4$ are each H or $C_{1-6}$alkyl or $R^3$ and $R^4$ together are linked so as to form a $C_{1-3}$alkylene chain; $R^5$ represents H, $C_{1-6}$alkyl, $C_{3-7}$cycloalkyl, $C_{3-7}$cycloalkyl$C_{1-4}$alkyl, phenyl$C_{1-4}$alkyl, $CO_2R^a$, $CONR^aR^b$, $SOR^a$ or $SO_2R^a$, wherein the phenyl moiety may be substituted by $C_{1-6}$alkyl, $C_{1-6}$alkoxy, halogen or trifluoromethyl; X and Y are each H, or together represents =O; and Z represents a bond, O, S, SO, $SO_2$, $NR^6$, or —($CR^6R^6$)— where $R^6$ is H or $C_{1-6}$alkyl; or a pharmaceutically acceptable salt thereof. The compounds are of particular use in the treatment or prevention of pain, inflammation, migraine, emesis and postherpetic neuralgia.

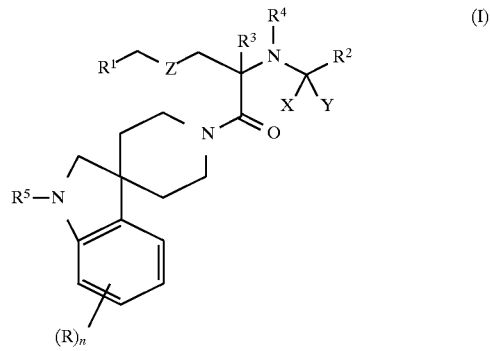

25 Claims, No Drawings

SPIRO-SUBSTITUTED AZACYCLIC DERIVATIVES AND THEIR USE AS THERAPEUTIC AGENTS

This application is 371 of PCT/GB95/08167 which is now published as WO 96/05203 on Feb. 22, 1995.

This invention relates to a class of spiro-substituted azacyclic compounds, which are useful as tachykinin antagonists. More particularly, the compounds of the invention comprise an azacyclic ring system spiro-substituted by an indolyl moiety and a substituted serine derived moiety.

The tachykinins are a group of naturally occurring peptides found widely distributed throughout mammalian tissues, both within the central nervous system and in peripheral nervous and circulatory systems.

At present, there are three known mammalian tachykinins referred to as substance P, neurokinin A (NKA, substance K, neuromedin L) and neurokinin B (NKB, neuromedin K) (for review see J. E. Maggio, *Peptides* (1985) 6(suppl. 3), 237–242). The current nomenclature designates the three tachykinin receptors mediating the biological actions of substance P, NKA and NKB as the $NK_1$, $NK_2$ and $NK_3$ receptors, respectively.

Evidence for the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases, proliferative vitreoretinopathy, irritable bowel syndrome and disorders of bladder function including cystitis and bladder detruser hyper-reflexia is reviewed in "Tachykinin Receptors and Tachykinin Receptor Antagonists", C. A. Maggi, R. Patacchini, P. Rovero and A. Giachetti, *J. Auton. Pharmacol.* (1993) 13, 23–93.

For instance, substance P is believed inter alia to be involved in the neurotransmission of pain sensations [Otsuka et al, "Role of Substance P as a Sensory Transmitter in Spinal Cord and Sympathetic Ganglia" in 1982 Substance P in the Nervous System, Ciba Foundation Symposium 91, 13–34 (published by Pitman) and Otsuka and Yanagisawa, "Does Substance P Act as a Pain Transmitter?" *TIPS* (1987) 8, 506–510], specifically in the transmission of pain in migraine (B. E. B. Sandberg et al, *J. Med Chem*, (1982) 25, 1009) and in arthritis [Levine et al in *Science* (1984) 226, 547–549]. Tachykinins have also been implicated in gastrointestinal (GI) disorders and diseases of the GI tract such as inflammatory bowel disease [Mantyh et al in *Neuroscience* (1988) 25(3), 817–37 and D. Regoli in "Trends in Cluster Headache" Ed. Sicuteri et al Elsevier Scientific Publishers, Amsterdam (1987) page 85)] and emesis [F. D. Tattersall et al, *Eur. J. Pharmacol.*, (1993) 250, $R^5$–$R^6$]. It is also hypothesised that there is a neurogenic mechanism for arthritis in which substance P may play a role [Kidd et al "A Neurogenic Mechanism for Symmetrical Arthritis" in *The Lancet*, 11 Nov. 1989 and Grönblad et al, "Neuropeptides in Synovium of Patients with Rheumatoid Arthritis and Osteoarthritis" in *J. Rheumatol.* (1988) 15(12), 1807–10]. Therefore, substance P is believed to be involved in the inflammatory response in diseases such as rheumatoid arthritis and osteoarthritis, and fibrositis [O'Byrne et al, *Arthritis and Rheumatism* (1990) 33, 1023–8]. Other disease areas where tachykinin antagonists are believed to be useful are allergic conditions [Hamelet et al, *Can. J. Pharmacol. Physiol.* (1988) 66, 1361–7], immunoregulation [Lotz et al, *Science* (1988) 241, 1218–21 and Kimball et al, *J. Immunol.* (1988) 141(10), 3564–9] vasodilation, bronchospasm, reflex or neuronal control of the viscera [Mantyh et al, *PNAS* (1988) 85, 3235–9] and, possibly by arresting or slowing β-amyloid-mediated neurodegenerative changes [Yankner et al, *Science* (1990) 250, 279–82] in senile dementia of the Alzheimer type, Alzheimer's disease and Down's Syndrome.

Tachykinin antagonists may also be useful in the treatment of small cell carcinomas, in particular small cell lung cancer (SCLC) [Langdon et al, *Cancer Research* (1992) 52, 4554–7].

Substance P may also play a role in demyelinating diseases such as multiple sclerosis and amyotrophic lateral sclerosis [J. Luber-Narod et al, poster C.I.N.P. XVIIIth Congress, 28th Jun.–2nd Jul. 1992], and in disorders of bladder function such as bladder detrusor hyper-reflexia (*Lancet*, 16th May 1992, 1239).

It has furthermore been suggested that tachykinins have utility in the following disorders: depression, dysthymic disorders, chronic obstructive airways disease, hypersensitivity disorders such as poison ivy, vasospastic diseases such as angina and Reynauld's disease, fibrosing and collagen diseases such as scleroderma and eosinophilic fascioliasis, reflex sympathetic dystrophy such as shoulder/hand syndrome, addiction disorders such as alcoholism, stress related somatic disorders, neuropathy, neuralgia, disorders related to immune enhancement or suppression such as systemic lupus erythmatosus European patent specification no. 0 436 334), ophthalmic disease such as conjuctivitis, vernal conjunctivitis, and the like, and cutaneous diseases such as contact dermatitis, atopic dermatitis, urticaria, and other eczematoid dermatitis (European patent specification no. 0 394 989).

In view of their metabolic instability, peptide derivatives are likely to be of limited utility as therapeutic agents. It is for this reason that non-peptide tachykinin antagonists are sought.

In essence, this invention provides a class of potent non-peptide tachykinin antagonists.

The present invention provides a compound of formula (I), or a pharmaceutically acceptable salt thereof:

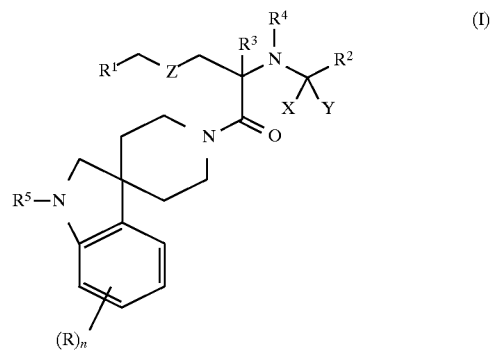

wherein n is zero, 1, 2 or 3;

R represents $C_{1-6}$alkyl, $C_{1-6}$alkoxy, hydroxy, halogen, cyano, trifluoromethyl, $SO_2C_{1-6}$alkyl, $NR^aR^b$, $NR^aCOR^b$, or $CONR^aR^b$, where $R^a$ and $R^b$ each independently represent hydrogen, $C_{1-6}$alkyl, phenyl or trifluoromethyl;

$R^1$ represents unsubstituted phenyl or phenyl substituted by 1, 2 or 3 groups selected from $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, —O(CH$_2$)$_p$O— where p is 1 or 2, halogen, cyano, nitro, trifluoromethyl, trimethylsilyl, OR$^a$, SR$^a$, SOR$^a$, SO$_2$R$^a$, NR$^a$R$^b$, NR$^a$COR$^b$, NR$^a$CO$_2$R$^b$, COR$^a$, CO$_2$R$^a$ or CONR$^a$R$^b$, where R$^a$ and R$^b$ are as previously defined; naphthyl; benzhydryl; or benzyl, where the naphthyl group or each phenyl moiety of benzyl and benzhydryl may be substituted by $C_{1-6}$alkyl, $C_{1-6}$alkoxy, halogen or trifluoromethyl;

R$^2$ represents hydrogen; unsubstituted phenyl or phenyl substituted by 1, 2 or 3 groups selected from $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, —O(CH$_2$)$_p$O— where p is 1 or 2, halogen, cyano, nitro, trifluoromethyl, trimethylsilyl, OR$^a$, SR$^a$, SOR$^a$, SO$_2$R$^a$, NR$^a$R$^b$, NR$^a$COR$^b$, NR$^a$CO$_2$R$^b$, COR$^a$, CO$_2$R$^a$, or CONR$^a$R$^b$, where R$^a$ and R$^b$ are as previously defined; heteroaryl selected from indazolyl, thienyl, furanyl, pyridyl, thiazolyl, tetrazolyl and quinolinyl; naphthyl; benzhydryl; or benzyl; wherein each heteroaryl, the naphthyl group and each phenyl moiety of benzyl and benzhydryl may be substituted by $C_{1-6}$alkyl, $C_{1-6}$alkoxy, halogen or trifluoromethyl;

R$^3$ and R$^4$ each independently represents hydrogen or $C_{1-6}$alkyl or R$^3$ and R$^4$ together are linked so as to form a $C_{1-3}$alkylene chain;

R$^5$ represents hydrogen, $C_{1-6}$alkyl, $C_{3-7}$cycloalkyl, $C_{3-7}$cycloalkyl$C_{1-4}$alkyl, phenyl$C_{1-4}$alkyl, CO$_2$R$^a$, CONR$^a$R$^b$, SOR$^a$ or SO$_2$R$^a$, wherein the phenyl moiety may be substituted by $C_{1-6}$alkyl, $C_{1-6}$alkoxy, halogen or trifluoromethyl, and R$^a$ and R$^b$ are as previously defined;

X and Y each independently represents hydrogen, or together form a group =O; and Z represents a bond, O, S, SO, SO$_2$, NR$^6$, or —(CR$^6$R$^6$)— where each R$^6$ is hydrogen or $C_{1-6}$alkyl.

As used herein, the definition of each expression, when it occurs more than once in any structure, is intended to be independent of its definition elsewhere in the same structure.

The alkyl, alkenyl and alkynyl groups referred to with respect to the formulae herein may represent straight or branched groups. Thus, for example, suitable alkyl groups include methyl, ethyl, n- or iso-propyl and n-, sec-, iso- or tert-butyl. The cycloalkyl groups referred to above may be, for example, cyclopropyl, cyclobutyl, cyclopentyl or cyclohexyl. Similarly, suitable cycloalkylalkyl groups include cyclopropylmethyl. Suitable alkenyl groups include vinyl and allyl; and suitable alkynyl groups include propargyl.

The term "halogen" as used herein includes fluorine, chlorine, bromine and iodine, especially chlorine and fluorine.

The present invention includes within its scope prodrugs of the compounds of formula (1) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

Those compounds according to the invention which contain one or more chiral centres may exist both as enantiomers and as diastereomers. It is to be understood that all such isomers and mixtures thereof are encompassed within the scope of the present invention.

Preferably n is zero.

Preferably R$^1$ represents unsubstituted phenyl or phenyl substituted by one or two groups selected from $C_{1-6}$alkyl such as methyl, halogen such as chlorine, fluorine and bromine, and trifluoromethyl. Particularly preferred substituents are chlorine and trifluoromethyl.

Most preferably, R$^1$ represents disubstituted phenyl, in particular 3,4-disubstituted phenyl, especially 3,4-dichlorophenyl.

Suitable values for the group R$^2$ include unsubstituted or substituted phenyl, 5-membered heteroaryl such as thienyl or furanyl, 6-membered heteroaryl such as pyridyl, quinolinyl, naphthyl, and benzhydryl.

Preferably R$^2$ represents unsubstituted or substituted phenyl, especially unsubstituted phenyl.

When R$^2$ represents substituted phenyl it preferably represents dichlorophenyl, especially 3,4-dichlorophenyl.

Preferably R$^3$ and R$^4$ each independently represent hydrogen.

Preferably R$^5$ represents the group SO$_2$R$^a$ where R$^a$ is as previously defined. Particularly preferred is the group SO$_2$($C_{1-6}$alkyl), especially SO$_2$CH$_3$.

Preferably X and Y are both hydrogen atoms.

Preferably Z is an oxygen atom.

In another preferred class of compounds of formula (I), Z is preferably —CH$_2$—.

A particular sub-class of compounds according to the invention is represented by compounds of formula (Ia), and pharmaceutically acceptable salts thereof.

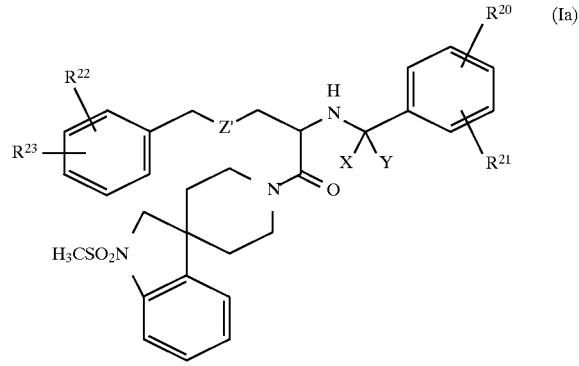

wherein

X and Y are as defined for formula (I);

Z' is O, S or —CH$_2$—, especially O or S;

R$^{20}$ and R$^{21}$ independently represent hydrogen, $C_{1-6}$alkyl, halogen, trifluoromethyl, OR$^a$, or NR$^a$R$^b$, where R$^a$ and R$^b$ are as previously defined; and R$^{22}$ and R$^{23}$ independently represent hydrogen or halogen, preferably hydrogen or chlorine.

Particular values of R$^{20}$ and R$^{21}$ include hydrogen, chlorine, fluorine, methyl, trifluoromethyl, methoxy and dimethylamino.

Another preferred sub-class of compounds according to the invention is represented by compounds of formula (Ib), and pharmaceutically acceptable salts thereof:

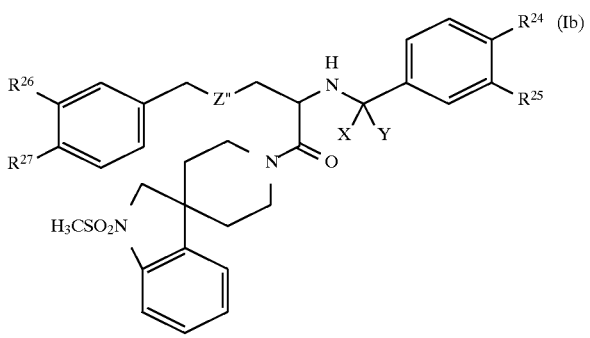

wherein

Z" is O or —CH$_2$—, especially O;

R$^{24}$ and R$^{25}$ independently represent hydrogen or chlorine; and

R$^{26}$ and R$^{27}$ independently represent hydrogen or chlorine, with the proviso that at least one of R$^{26}$ and R$^{27}$ represents chlorine.

Specific compounds within the scope of the present invention include:

N-[1-methanesulphonylspiro(3H-indole-3,4'-piperidin)-1-yl]-3-benzyloxy-2-(3,4-dichlorobenzamido)propionamide;

N-[1-methanesulphonylspiro(3H-indole-3,4'-piperidin)-1-yl]-3-benzyloxy-2-(3-pyridylcarboxamido)propionamide;

N-[1-methanesulphonylspiro(3H-indole-3,4'-piperidin)-1-yl]-3-benzyloxy-2-(2-chlorobenzamido)propionamide;

N-[1-methanesulphonylspiro(3H-indole-3,4'-piperidin)-1-yl]-3-benzyloxy-2-(3-chlorobenzamido)propionamide;

N-[1-methanesulphonylspiro(3H-indole-3,4'-piperidin)-1-yl]-3-benzyloxy-2-(4-chlorobenzamido)propionamide;

N-[1-methanesulphonylspiro(3H-indole-3,4'-piperidin)-1-yl]-3-benzyloxy-2-(2,6-dichlorobenzamido)propionamide;

N-[1-methanesulphonylspiro(3H-indole-3,4'-piperidin)-1-yl]-3-benzyloxy-2-(3,5-dichlorobenzamido)propionamide;

N-[1-methanesulphonylspiro(3H-indole-3,4'-piperidin)-1-yl]-3-benzyloxy-2-(2,5-dichlorobenzamido)propionamide;

N-[1-methanesulphonylspiro(3H-indole-3,4'-piperidin)-1-yl]-3-benzyloxy-2-(2,4-dichlorobenzamido)propionamide;

N-[1-methanesulphonylspiro(3H-indole-3,4'-piperidin)-1-yl]-3-benzyloxy-2-(2,3-dichlorobenzamido)propionamide;

N-[1-methanesulphonylspiro(3H-indole-3,4'-piperidin)-1-yl]-3-benzyloxy-2-(3,4-dimethoxybenzamido)propionamide;

N-[1-methanesulphonylspiro(3H-indole-3,4'-piperidin)-1-yl]-3-benzyloxy-2-benzamidopropionamide;

N-[1-methanesulphonylspiro(3H-indole-3,4'-piperidin)-1-yl]-3-benzyloxy-2-(3-(2-propyloxy)benzamido)propionamide;

N-[1-methanesulphonylspiro(3H-indole-3,4'-piperidin)-1-yl]-3-benzyloxy-2-[(1-naphthyl)carboxamido)]propionamide;

N-[1-methanesulphonylspiro(3H-indole-3,4'-piperidin)-1-yl]-3-benzyloxy-2-[(2-naphthyl)carboxamido)]propionamide;

N-[1-methanesulphonylspiro(3H-indole-3,4'-piperidin)-1-yl]-3-benzyloxy-2-(phenylacetamido)propionamide;

N-[1-methanesulphonylspiro(3H-indole-3,4'-piperidin)-1-yl]-3-benzyloxy-2-(3,4-dichlorophenylacetamido)propionamide;

N-[1-methanesulphonylspiro(3H-indole-3,4'-piperidin)-1-yl]-3-benzyloxy-2-[(3,5-bis(trifluoromethyl)phenyl)acetamido]propionamide;

N-[1-methanesulphonylspiro(3H-indole-3,4'-piperidin)-1-yl]-3-benzyloxy-2-(diphenylacetamido)propionamide;

N-[1-methanesulphonylspiro(3H-indole-3,4'-piperidin)-1-yl]-3-benzyloxy-2-(4-pyridylcarboxamido)propionamide;

N-[1-methanesulphonylspiro(3H-indole-3,4'-piperidin)-1-yl]-3-benzyloxy-2-(2-pyridylcarboxamido)propionamide;

N-[1-methanesulphonylspiro(3H-indole-3,4'-piperidin)-1-yl]-3-benzyloxy-2-(8-quinolinylcarboxamido)propionamide;

and pharmaceutically acceptable salts thereof

Particularly preferred compounds within the scope of the present invention include:

N-[1-methanesulphonylspiro(3H-indole-3,4'-piperidin)-1-yl]-3-benzyloxy-2-(3,4-dichlorobenzylamino)propionamide;

N-[1-methanesulphonylspiro(3H-indole-3,4'-piperidin)-1-yl]-3-benzyloxy-2-(2-methoxybenzylamino)propionamide;

N-[1-methanesulphonylspiro(3H-indole-3,4'-piperidin)-1-yl]-2-benzylamino-3-benzyloxypropionamide;

N-[1-methanesulphonylspiro(3H-indole-3,4'-piperidin)-1-yl]-3-benzyloxy-2-(2-chlorobenzylamino)propionamide;

N-[1-methanesulphonylspiro(3H-indole-3,4'-piperidin)-1-yl]-3-benzyloxy-2-(3-chlorobenzylamino)propionamide;

N-[1-methanesulphonylspiro(3H-indole-3,4'-piperidin)-1-yl]-3-benzyloxy-2-(4-chlorobenzylamino)propionamide;

N-[1-methanesulphonylspiro(3H-indole-3,4'-piperidin)-1-yl]-3-benzyloxy-2-(3-bromobenzylamino)propionamide;

N-[1-methanesulphonylspiro(3H-indole-3,4'-piperidin)-1-yl]-3-benzyloxy-2-(3-fluorobenzylamino)propionamide;

N-[1-methanesulphonylspiro(3H-indole-3,4'-piperidin)-1-yl]-3-benzyloxy-2-(3-cyanobenzylamino)propionamide;

N-[1-methanesulphonylspiro(3H-indole-3,4'-piperidin)-1-yl]-3-benzyloxy-2-(3-nitrobenzylamino)propionamide;

N-[1-methanesulphonylspiro(3H-indole-3,4'-piperidin)-1-yl]-3-benzyloxy-2-(3-methylbenzylamino)propionamide;

N-[1-methanesulphonylspiro(3H-indole-3,4'-piperidin)-1-yl]-3-benzyloxy-2-(3-methoxybenzylamino)propionamide;

N-[1-methanesulphonylspiro(3H-indole-3,4'-piperidin)-1-yl]-3-benzyloxy-2-(4-methoxybenzylamino)propionamide;

N-[1-methanesulphonylspiro(3H-indole-3,4'-piperidin)-1-yl]-3-benzyloxy-2-(4-(dimethylamino)benzylamino)propionamide;

N-[1-methanesulphonylspiro(3H-indole-3,4'-piperidin)-1-yl]-3-benzyloxy-2-(2,4-dichlorobenzylamino)propionamide;

N-[1-methanesulphonylspiro(3H-indole-3,4'-piperidin)-1-yl]-3-benzyloxy-2-(3,5 -dichlorobenzylamino)propionamide;

N-[1-methanesulphonylspiro(3H-indole-3,4'-piperidin)-1-yl]-3-benzyloxy-2-(2,3-dichlorobenzylamino)propionamide;

N-[1-methanesulphonylspiro(3H-indole-3,4'-piperidin)-1-yl]-3-benzyloxy-2-(2,6-dichlorobenzylamino)propionamide;

N-[1-methanesulphonylspiro(3H-indole-3,4'-piperidin)-1-yl]-3-benzyloxy-2-(3,5-dimethoxybenzylamino)propionamide;

N-[1-methanesulphonylspiro(3H-indole-3,4'-piperidin)-1-yl]-3-benzyloxy-2-(3-chloro-5-methoxybenzylamino)propionamide;

N-[1-methanesulphonylspiro(3H-indole-3,4'-piperidin)-1-yl]-3-benzyloxy-2-(3,4-dimethoxybenzylamino)propionamide;
N-[1-methanesulphonylspiro(3H-indole-3,4'-piperidin)-1-yl]-3-benzyloxy-2-(3,4-methylenedioxybenzylamino)propionamide;
N-[1-methanesulphonylspiro(3H-indole-3,4'-piperidin)-1-yl]-3-benzyloxy-2-(1-naphthylmethylamino)propionamide;
N-[1-methanesulphonylspiro(3H-indole-3,4'-piperidin)-1-yl]-3-benzyloxy-2-(2-naphthylmethylamino)propionamide;
N-[1-methanesulphonylspiro(3H-indole-3,4'-piperidin)-1-yl]-3-benzyloxy-2-(2-pyridylmethylamino)propionamide;
N-[1-methanesulphonylspiro(3H-indole-3,4'-piperidin)-1-yl]-3-benzyloxy-2-(3-pyridylmethylamino)propionamide;
N-[1-methanesulphonylspiro(3H-indole-3,4'-piperidin)-1-yl]-3-benzyloxy-2-(4-pyridylmethylamino)propionamide;
N-[1-methanesulphonylspiro(3H-indole-3,4'-piperidin)-1-yl]-3-benzyloxy-2-(2-furylmethylamino)propionamide;
N-[1-methanesulphonylspiro(3H-indole-3,4'-piperidin)-1-yl]-3-benzyloxy-2-[(5-methylfur-2-yl)methylamino]propionamide;
N-[1-methanesulphonylspiro(3H-indole-3,4'-piperidin)-1-yl]-3-benzyloxy-2-[(3-methylthiophen-2-yl)methylamino]propionamide;
N-[1-methanesulphonylspiro(3H-indole-3,4'-piperidin)-1-yl]-3-benzyloxy-2-[(5-methylthiophen-2-yl)methylamino]propionamide;
N-[1-methanesulphonylspiro(3H-indole-3,4'-piperidin)-1-yl]-3-benzyloxy-2-(N-(3,4-dichlorobenzyl)-N-(methyl)amino)propionamide;
N-[1-methanesulphonylspiro(3H-indole-3,4'-piperidin)-1-yl]-2-benzylamino-3-(2-chlorobenzyloxy)propionamide;
N-[1-methanesulphonylspiro(3H-indole-3,4'-piperidin)-1-yl]-2-benzylamino-3-(3-chlorobenzyloxy)propionamide;
N-[1-methanesulphonylspiro(3H-indole-3,4'-piperidin)-1-yl]-2-benzylamino-3-(4-chlorobenzyloxy)propionamide;
N-[1-methanesulphonylspiro(3H-indole-3,4'-piperidin)-1-yl]-3-(2-chlorobenzyloxy)-2-(3,4-dichlorobenzylamino)propionamide;
N-[1-methanesulphonylspiro(3H-indole-3,4'-piperidin)-1-yl]-3-(3-chlorobenzyloxy)-2-(3,4-dichlorobenzylamino)propionamide;
N-[1-methanesulphonylspiro(3H-indole-3,4'-piperidin)-1-yl]-3-(4-chlorobenzyloxy)-2-(3,4-dichlorobenzylamino)propionamide;
N-[1-methanesulphonylspiro(3H-indole-3,4'-piperidin)-1-yl]-3-(benzylthio)-2-(3,4-dichlorobenzylamino)propionamide;
N-[1-methanesulphonylspiro(3H-indole-3,4'-piperidin)-1-yl]-2-benzylamino-3-(3,4-dichlorobenzyloxy)propionamide;
N-[1-methanesulphonylspiro(3H-indole-3,4'-piperidin)-1-yl]-3-(3,4-dichlorobenzyloxy)-2-(3,4-dichlorobenzylamino)propionamide;
and pharmaceutically acceptable salts thereof.

Further preferred compounds of the present invention include:
N-[1-methanesulfonylspiro(3H-indole-3,4'-piperidin)-1-yl]-2-(benzylamino)-3-[(napth-2-yl)methoxy]propionamide;
N-[1-methanesulfonylspiro(3H-indole-3,4'-piperidin)-1-yl]-2-(benzylamino)-3-[(napth-1-yl)methoxy]propionamide;
N-[1-methanesulfonylspiro(3H-indole-3,4'-piperidin)-1-yl]-2-[N-(methyl)benzylamino]-3-(3,4-dichlorobenzyloxy)propionamide;
N-[1-methanesulfonylspiro(3H-indole-3,4'-piperidin)-1-yl]-3-(3,4-dichlorobenzyloxy)-2-(dimethyl)aminopropionamide;
N-[1-methanesulfonylspiro(3H-indole-3,4'-piperidin)-1-yl]-3-(3,4-dichlorobenzylthio)-2-(benzylamino)propionamide;
N-[1-methanesulfonylspiro(3H-indole-3,4'-piperidin)-1-yl]-3-(3,4-dichlorobenzylsulfonyl)-2-(benzylamino)propionamide;
N-[1-methanesulfonylspiro(3H-indole-3,4'-piperidin)-1-yl]-2,3-bis(benzylamino)propionamide;
N-[1-methanesulfonylspiro(3H-indole-3,4'-piperidin)-1-yl]-2-(benzylamino)-3-(3,4-dichlorobenzylamino)propionamide;
N-[1-methanesulfonylspiro(3H-indole-3,4'-piperidin)-1-yl]-2-(benzylamino)-3-(N-methyl-3,4-dichlorobenzylamino)propionamide;
N-[1-methanesulfonylspiro(3H-indole-3,4'-piperidin)-1-yl]-2-(benzylamino)-5-phenylpentanamide;
N-[1-methanesulfonylspiro(3H-indole-3,4'-piperidin)-1-yl]-2-(benzylamino)-5-(3,4-dichlorophenyl)pentanamide;
N-[1-methanesulfonylspiro(3H-indole-3,4'-piperidin)-1-yl]-2-(benzylamino)-5-(3,4-dichlorophenyl)butanamide;
and pharmaceutically acceptable salts thereof Especially preferred compounds of the present invention include:
N-[1-methanesulfonylspiro(3H-indole-3,4'-piperidin)-1-yl]-2-(benzylamino)-3-(3,4-dichlorobenzyloxy)propionamide;
N-[1-methanesulfonylspiro(3H-indole-3,4'-piperidin)-1-yl]-2-(3,4-dichlorobenzylamino)-3-(3,4-dichlorobenzyloxy)propionaamide;
and pharmaceutically acceptable salts thereof.

For use in medicine, the salts of the compounds of formula (I) will be pharmaceutically acceptable salts. Other salts may, however, be useful in the preparation of the compounds according to the invention (such as the dibenzoyltartrate salts) or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable non-toxic acid such as hydrochloric acid, sulphuric acid, fumaric acid, maleic acid, succinic acid, acetic acid, citric acid, tartaric acid, carbonic acid, phosphoric acid or p-toluenesulphonic acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

Preferred salts of the compounds according to the invention include the hydrochloride and p-toluenesulphonic acid salts.

The invention also provides pharmaceutical compositions comprising one or more compounds of this invention in association with a pharmaceutically acceptable carrier. Preferably these compositions are in unit dosage forms such as tablets, pills, capsules, powders, granules, solutions or suspensions, or suppositories, for oral, parenteral or rectal administration, or topical administration including administration by inhalation or insufflation.

The invention further provides a process for the preparation of a pharmaceutical composition comprising a compound of formula (I), or a salt or prodrug thereof, and a pharmaceutically acceptable carrier, which process comprises bringing a compound of formula (I), or a salt or prodrug thereof into association with a pharmaceutically acceptable carrier.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Preferred compositions for administration by injection include those comprising a compound of formula (I), as the active ingredient, in association with a surface-active agent (or wetting agent or surfactant) or in the form of an emulsion (as a water-in-oil or oil-in-water emulsion).

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and preferably between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a premixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example gylcerol or glucose, to adjust the tonicity of the emulsion. Suitable emulsions will typically contain up to 20% oil, for example, between 5 and 20%. The fat emulsion will preferably comprise fat droplets between 0.1 and 1.0 $\mu$m, particularly 0.1 and 0.5 $\mu$m, and have a pH in the range of 5.5 to 8.0.

Particularly preferred emulsion compositions are those prepared by mixing a compound of formula (I) with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

The present invention further provides a process for the preparation of a pharmaceutical composition comprising a compound of formula (I), which process comprises bringing a compound of formula (I) into association with a pharmaceutically acceptable carrier or excipient.

The compounds of formula (I) are of value in the treatment of a wide variety of clinical conditions which are characterised by the presence of an excess of tachykinin, in particular substance P, activity. These may include disorders of the central nervous system such as anxiety, depression, psychosis and schizophrenia; epilepsy; neurodegenerative disorders such as dementia, including AIDS related dementia, senile dementia of the Alzheimer type, Alzheimer's disease and Down's syndrome; demyelinating diseases such as multiple sclerosis OS) and amyotrophic lateral sclerosis (ALS; Lou Gehrig's disease) and other neuropathological disorders such as peripheral neuropathy, for example AIDS related neuropathy, diabetic and chemotherapy-induced neuropathy, and postherpetic and other neuralgias; neuronal damage, such as cerebralischemic damage and cerebral edema in cerebrovascular disorders; small cell carcinomas such as small cell lung cancer; respiratory diseases, particularly those associated with excess mucus secretion such as chronic obstructive airways disease, bronchopneumonia, chronic bronchitis, asthma, and bronchospasm; airways diseases modulated by neurogenic inflammation; diseases characterised by neurogenic mucus secretion, such as cystic fibrosis; diseases associated with decreased glandular secretions, including lacrimation, such as Sjogren's syndrome, hyperlipoproteinemias IV and V, hemocromatosis, sarcoidosis, and amyloidosis; inflammatory diseases such as inflammatory bowel disease, psoriasis, fibrositis, ocular inflammation, osteoarthritis, rheumatoid arthritis, pruritis and sunburn; allergies such as eczema and rhinitis; hypersensitivity disorders such as poison ivy; ophthalmic diseases such as conjunctivitis, vernal conjunctivitis, dry eye syndrome, and the like; ophthalmic conditions associated with cell proliferation such as proliferative vitreoretinopathy; cutaneous diseases such as contact dermatitis, atopic dermatitis, urticaria, and other eczematoid dermatitis;

addiction disorders including the withdrawal response produced by chronic treatment with, or abuse of, drugs such as benzodiazepines, opiates, cocaine, alcohol and nicotine; stress related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosus; gastrointestinal (GI) disorders, including inflammatory disorders and diseases of the GI tract such as gastritis, gastroduodenal ulcers, gastric carcinomas, gastric lymphomas, disorders associated with the neuronal control of viscera, ulcerative colitis, Crohn's disease, irritable bowel syndrome and emesis, including acute, delayed, post-operative, late phase or anticipatory emesis such as emesis induced by chemotherapy, radiation, toxins, viral or bacterial infections, pregnancy, vestibular disorders, motion, surgery, migraine, opioid analgesics, and variations in intercranial pressure, in particular, for example, drug or radiation induced emesis or post-operative nausea and vomiting; disorders of bladder function such as cystitis, bladder detrusor hyper-reflexia and incontinence; fibrosing and collagen diseases such as scleroderma and eosinophilic fascioliasis; disorders of blood flow caused by vasodilation and vasospastic diseases such as angina, migraine and Reynaud's disease; and pain or nociception, for example, that attributable to or associated with any of the foregoing conditions, especially the transmission of pain in migraine.

Hence, the compounds of the present invention may be of use in the treatment of physiological disorders associated with excessive stimulation of tachykinin receptors, especially neurokinin-1 receptors, and as neurokinin-1 antagonists for the control and/or treatment of any of the aforementioned clinical conditions in mammals, including humans.

The compounds of formula (I) are also of value in the treatment of a combination of the above conditions, in particular in the treatment of combined post-operative pain and post-operative nausea and vomiting.

The compounds of formula (I) are particularly useful in the. treatment of emesis, including acute, delayed, post-operative, late phase or anticipatory emesis, such as emesis or nausea induced by chemotherapy, radiation, toxins, such as metabolic or microbial toxins, viral or bacterial infections, pregnancy, vestibular disorders, motion, mechanical stimulation, gastrointestinal obstruction, reduced gatrointestinal motility, visceral pain, psychological stress or disturbance, high altitude, weightlessness, opioid analgesics, intoxication, resulting for example from consumption of alcohol, surgery, migraine, and variations in intercranial pressure. Most especially, the compounds of formula (I) are of use in the treatment of emesis induced by antineoplastic (cytotoxic) agents including those routinely used in cancer chemotherapy.

Examples of such chemotherapeutic agents include alkylating agents, for example, nitrogen mustards, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; and cytotoxic antibiotics.

Particular examples of chemotherapeutic agents are described, for instance, by D. J. Stewart in *"Nausea and Vomiting:* Recent Research and *Clinical Advances"*, Eds. J. Kuucharczyk et al, CRC Press Inc., Boca Raton, Fla., U.S.A. (1991) pages 177–203, especially page 188. Commonly used chemotherapeutic agents include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin and chlorambucil [R. J. Gralla et al in *Cancer Treatment Reports* (1984) 68(1), 163–172].

The compounds of formula (I) are also of use in the treatment of emesis induced by radiation including radiation therapy such as in the treatment of cancer, or radiation sickness; and in the treatment of post-operative nausea and vomiting.

It will be appreciated that the compounds of formula (I) may be presented together with another therapeutic agent as a combined preparation for simultaneous, separate or sequential use for the relief of emesis. Such combined preparations may be, for example, in the form of a twin pack.

A further aspect of the present invention comprises the compounds of formula (I) in combination with a 5-HT$_3$ antagonist, such as ondansetron, granisetron or tropisetron, or other anti-emetic medicaments, for example, a dopamine antagonist such as metoclopramide or GABA$_B$ receptor agonists such as baclofen. Additionally, a compound of formula (I) may be administered in combination with an anti-inflammatory corticosteroid, such as dexamethasone, triamcinolone, triamcinolone acetonide, flunisolide, budesonide, or others such as those disclosed in U.S. Pat. Nos. 2,789,118, 2,990,401, 3,048,581, 3,126,375, 3,929,768, 3,996,359, 3,928,326 and 3,749,712. Dexamethasone (Decadron™) is particularly preferred. Furthermore, a compound of formula (I) may be administered in combination with a chemotherapeutic agent such as an alkylating agent, antimetabolite, mitotic inhibitor or cytotoxic antibiotic, as described above. In general, the currently available dosage forms of the known therapeutic agents for use in such combinations will be suitable.

When tested in the ferret model of cisplatin-induced emesis described by F. D. Tattersall et al, in *Eur. J. pharmacol.*, (1993) 250, R5–R6, the compounds of the present invention were found to attenuate the retching and vomiting induced by cisplatin.

The compounds of formula (I) are also particularly useful in the treatment of pain or nociception and/or inflammation and disorders associated therewith such as, for example, neuropathy, such as-diabetic and chemotherapy-induced neuropathy, postherpetic and other neuralgias, asthma, osteoarthritis, rheumatoid arthritis, headache and especially migraine.

The present invention further provides a compound of formula (I) for use in therapy.

According to a further or alternative aspect, the present invention provides a compound of formula (I) for use in the manufacture of a medicament for the treatment of physiological disorders associated with an excess of tachykinins, especially substance P.

The present invention also provides a method for the the treatment or prevention of physiological disorders associated with an excess of tachykinins, especially substance P, which method comprises administration to a patient in need thereof of a tachykinin reducing amount of a compound of formula (I) or a composition comprising a compound of formula (I).

For the treatment of certain conditions it may be desirable to employ a compound according to the present invention in conjunction with another pharmacologically active agent. For example, for the treatment of respiratory diseases such as asthma, a compound of formula (I) may be used in conjunction with a bronchodilator, such as a $\beta_2$-adrenergic receptor antagonist or tachykinin antagonist which acts at NK-2 receptors. The compound of formula (I) and the bronchodilator may be administered to a patient simultaneously, sequentially or in combination.

Likewise, a compound of the present invention may be employed with a leukotriene antagonists, such as a leukotriene $D_4$ antagonist such as a compound selected from those disclosed in European patent specification nos. 0 480 717 and 0 604 114 and in U.S. Pat. Nos. 4,859,692 and 5,270,324. This combination is particularly useful in the treatment of respiratory diseases such as asthma, chronic bronchitis and cough.

The present invention accordingly provides a method for the treatment of a respiratory disease, such as asthma, which method comprises administration to a patient in need thereof of an effective amount of a compound of formula (I) and an effective amount of a bronchodilator.

The present invention also provides a composition comprising a compound of formula (I), a bronchodilator, and a pharmaceutically acceptable carrier.

It will be appreciated that for the treatment or prevention of migraine, a compound of the present invention may be used in conjunction with other anti-migraine agents, such as ergotamines or 5-$HT_1$ agonists, especially sumatriptan.

Likewise, for the treatment of behavioural hyperalgesia, a compound of the present invention may be used in conjunction with an antagonist of N-methyl D-aspartate (NMDA), such as dizocilpine.

For the treatment or prevention of inflammatory conditions in the lower urinary tract, especially cystitis, a compound of the present invention may be used in conjunction with an antiinflammatory agent such as a bradykinin receptor antagonist.

In the treatment of the conditions associated with an excess of tachykinins, a suitable dosage level is about 0.001 to 50 mg/kg per day, in particular about 0.01 to about 25 mg/kg, such as from about 0.05 to about mg/kg per day.

For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

In the treatment of emesis using an injectable formulation, a suitable dosage level is about 0.001 to 10 mg/kg per day, preferably about 0.005 to 5 mg/kg per day, and especially 0.01 to 1 mg/kg per day. The compounds may be administered on a regimen of 1 to 4 times per day, preferably once or twice per day.

It will be appreciated that the amount of a compound of formula (I) required for use in any treatment will vary not only with the particular compounds or composition selected but also with the route of administration, the nature of the condition being treated, and the age and condition of the patient, and will ultimately be at the discretion of the attendant physician.

According to process (A), compounds of formula (I) wherein X and Y are both hydrogen, may be prepared from compounds of formula (II):

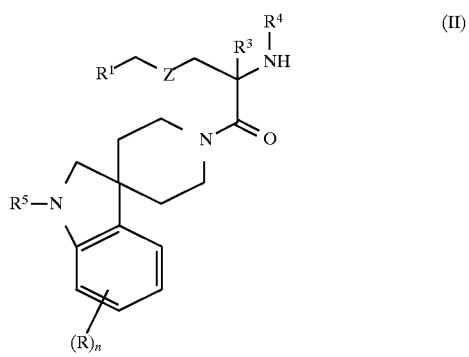

wherein R, $R^1$, $R^3$, $R^4$, $R^5$, Z and n are as defined for formula (I), by reaction with an aldehyde of formula $R^2$—CHO in the presence of a reducing agent.

Suitable reducing agents of use in the reaction include hydride reducing agents such as sodium cyanoborohydride or sodium borohydride.

The reaction is conveniently effected in a suitable solvent such as dimethylformamide or dichloromethane, conveniently at room temperature.

According to a process (B), compounds of formula (I) wherein X and Y together form a group =O, may be prepared by the reaction of a compound of formula (II) with an acyl halide of formula $R^2$—COHal where Hal is a halogen atom. typically chlorine, fluorine or bromine, especially chlorine.

The reaction is conveniently effected in the presence of an acylation catalyst such as 4-dimethylaminopyridine in a suitable solvent such as dichloromethane at a temperature between –10° C. and 40° C., conveniently at room temperature.

According to a further process (C), compounds of formula (I) may be prepared by the reaction of a compound of formula (III) with a piperidinyl derivative of formula (IV):

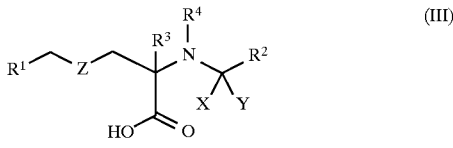

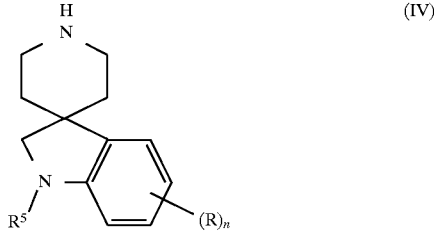

wherein R, $R^1$, $R^2$, $R^3$, $R^4$, $R^5$, X, Y, Z and n are as defined for formula (I) with the proviso that $R^5$ is not hydrogen.

The reaction is effected in the presence of a suitable coupling agent, such as dicyclocarbonyldiimide, N,N'-carbonyldiimide or 1-(3-dimethylaminopropyl)-3-ethylcarbodiimide optionally in the presence of an additive such as 1-hydroxybenzotriazole.

The reaction is conveniently effected in a suitable solvent such as dimethylformamide, conveniently at room temperature.

Further useful synthetic methods are those commonly used in standard syntheses of amino acids, for example, as described in *Chemistry and Biochemistry of the Amino Acids,* Ed. G. C. Barrett, Chapman and Hall, London 1985.

Compounds of formula (II) may be prepared from a suitably protected compound of formula (V):

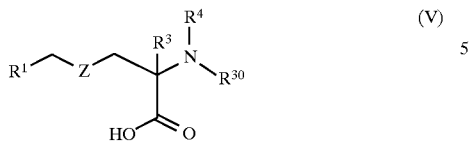

wherein $R^1$, $R^3$, $R^4$, and Z are as defined for formula (I) and $R^{30}$ is an amine protecting group, for example, tert-butoxycarbonyl (t-BOC), by reaction with a compound of formula (V) using the conditions of process (C), followed by deprotection in a conventional manner, for instance using hydrogen chloride in methanol.

Compounds of formula (III) may be prepared from a deprotected derivative corresponding to a compound of formula (V) by reaction with an aldehyde of formula $R^2$—CHO under the conditions of process (A) or an acyl halide of formula $R^2$—COHal under the conditions of process (B).

Compounds of formula (V) may be prepared by reaction of a compound of formula (VI):

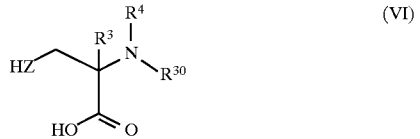

wherein $R^3$, $R^4$, and Z are as defined for formula (I) and $R^{30}$ is a protecting group as defined above, by reaction with a compound of the formula $R^1$—$CH_2L$, where L is a leaving group, for example, a halogen atom such as chlorine, bromine or iodine, or an alkyl- or arylsulphonyloxy group such as a mesylate or tosylate group. The reaction is effected in the presence of a suitable base, for example, an alkali metal hydride such as sodium hydride.

Compounds of formula (VI) are commercially available or may be prepared by known procedures.

Where the above-described process for the preparation of the compounds according to the invention gives rise to mixture of stereoisomers these isomers may, if desired, be separated, suitably by conventional techniques such as preparative chromatography.

The novel compounds which contain one or more chiral centres may be prepared in racemic form, or individual enantiomers may be prepared either by enantiospecific synthesis or by resolution.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The exemplified compounds of the invention were tested by the methods set out at pages 82 to 85 of International Patent Specification No. 93/04040. The compounds were found to be active with $IC_{50}$ at the $NK_1$ receptor of less than 300 nM.

The compounds of this invention may be formulated as specifically illustrated at pages 81 to 82 of International Patent Specification No. 93/04040.

The following Examples illustrate the preparation of compounds according to the invention.

DESCRIPTION 1

N-[1-methanesulfonylspiro(3H-indole-3,4'-piperidin)-1-yl]-3-benzyloxy-2-(t-butoxycarbonylamino)propionamide To N-tert-butoxycarbonyl-O-benzyl-d,l-serine (2.9 g, 9.83 mmol), and 1-hydroxybenzotriazole (278 mg), was added dry dimethylformamide (30 ml), and the mixture cooled to 4° C. 1-(3-Dimethylaminopropyl)-3-ethyl-carbodiimide hydrochloride (2.36 g) was added, and the resulting mixture stirred for 1 hour at room temperature. The resulting solution was then cooled to −15° C. and 1-methanesulfonylspiro(3H-indole-3,4'-piperidine) hydrochloride (2.93 g) was then added, followed after stirring for 5 minutes, by triethylamine (1.50 ml). The resulting mixture was warmed to room temperature, stirred at room temperature for 1.5 hours, then diluted with ethyl acetate (150 ml), washed with water (100 ml), and saturated aqueous sodium hydrogen carbonate (50 ml). The organic layer was dried over sodium sulfate, filtered, and solvents evaporated at reduced pressure. The residue was subjected to chromatogrmphy on silica gel (eluent 5% methanol/dichloromethane) to afford the title compound as a colourless solid. m/e ($Cl^+$) 544 ($MH^+$). m.p. 53°–56° C.

DESCRIPTION 2

N-[1-methanesulfonylspiro(3H-indole-3,4'-piperidin)-1-yl]-2-amino-3-benzyloxypropionamide hydrochloride To the product of Description 1 (0.48 g, 1 mmol), was added a saturated solution of hydrogen chloride in methanol (150 ml). The resulting solution was allowed to stand at room temperature for 24 hours. After evaporation of the volatiles at reduced pressure, the residue was dissolved in dichloromethane (50 ml), then diluted with diethyl ether (150 ml). Trituration of the mixture afforded the title compound as a colourless solid, recovered by filtration. Found: C, 56.65; H, 6.62; N, 8.45. $C_{23}H_{29}N_3O_4S.HCl.0.5(H_2O)$ requires: C, 56.48 H, 6.39; N, 8.59%. m/e ($Cl^+$) 444 ($MH^+$).

EXAMPLE 1

N-[1-methanesulfonylspiro(3H-indole-3,4'-piperidin)-1-yl]-3-benzyloxy-2-(3,4-dichlorobenzamido)propionanmide To the product of Description 2 (1.15 g, 2.4 mmol), dissolved in dry dichloromethane (5 ml), stirred at 4° C., was added triethylamine (0.700 ml), followed by 3,4-dichlorobenzoyl chloride (552 mg), and 4-dimethylaminopyridine (10 mg). The resulting mixture was warmed to room temperature and then stirred for a further 3 hours. The reaction mixture was diluted with ethyl acetate (50 ml) and washed with saturated aqueous sodium hydrogen carbonate (50 ml). The organic layer was dried over sodium sulfate, filtered, and solvents evaporated at reduced pressure. The residue was subjected to chromatography on silica gel (eluent 5% methanol/dichloromethane) to afford the title compound as a colourless foam. Found: C, 58.71; H, 5.06; N, 6.74. $C_{30}H_{31}N_3O_5SCl$ requires: C, 58.44 H, 5.07; N, 6.85%. m/e ($Cl^+$) 616 ($MH^+$).

EXAMPLE 2

N-[1-methanesulfonylspiro(3H-indole-3,4'-piperidin)-1-yl-3-benzyloxy-2-(3,4-dichlorobenzyl-amino)propionamide hydrochloride a) N-[1-methanesulfonylspiro(3H-indole-3,4'-piperidin)-1-yl]-3-benzyloxy-2-amino propionamide The product of Description 2 was stirred vigorously with saturated aqueous sodium carbonate and ethyl acetate for 30 minutes. The organic layer was then separated, dried over sodium sulfate, filtered, and solvents evaporated at reduced pressure to afford the title compound.

b) N[1-methanesulfonylspiro(3H-indole-3,4'-piperidin)-1-yl]-3-benzyloxy-2-(3,4-dichlorobenzylamino)propionamide hydrochloride To the product of step (a) (590 mg, 1.33 mmol), dissolved in dry dichloromethane (2.5 ml), was added 3,4-dichlorobenzaldehyde (260 mg), and anhydrous magnesium sulfate (1.3 g). The resulting mixture was stirred for 18 hours, then diluted with dichloromethane (50 ml) filtered and the solvents evaporated at reduced pressure. The residue was dissolved in methanol (3 ml) and sodium borohydride (55 mg) added with stirring. The resulting mixture was stirred for 1 hour at room temperature, and the solvents evaporated at reduced pressure. The residue was partitioned between water (15 ml) and ethyl acetate (25 ml). The organic layer was separated, dried over sodium sulfate, filtered, and solvents evaporated at reduced pressure. The residue was subjected to chromatography on silica gel (eluent 2.5% methanol/dichloromethane) to afford a colourless foam. This was dissolved in ethyl acetate, and treated with a saturated solution of hydrogen chloride in ether. The title compound was isolated by filtration as a colourless solid. Found: C, 56.64; H, 5.25; N, 6.61. $C_{30}H_{33}N_3O_4SCl_2.HCl$ requires: C, 56.39 H, 5.36; N, 6.58% m/e (CI$^+$) 602 (MH$^+$).

EXAMPLE 3

N-[1-methanesulfonylspiro(3H-indole-3,4'-piperidin)-1-yl]-3-benzyloxy-2-(3-pyridylcarboxamido)propionamide To nicotinic acid (77 mg), and 1-hydroxybenzotriazole (85 mg), in dry dimethylformamide (2.5 ml), was added 1-(3-dimethylaminopropyl)-3-ethyl-carbodiimide hydrochloride (120 mg), and the resulting mixture stirred for 1 hour at room temperature. Triethylamine (0.087 ml) was then added, followed by the product of Description 2 (300 mg). The resulting mixture was stirred at room temperature for 16 hours, then diluted with ethyl acetate (50 ml), washed with water (100 ml), and saturated aqueous sodium hydrogen carbonate (25 ml). The organic layer was dried over sodium sulfate, filtered, and solvents evaporated at reduced pressure. The residue was subjected to chromatography on silica gel (eluent ethyl acetate) to afford the title compound as a colourless solid. m/e (CI$^+$) 549 (MH$^+$). m.p. 80°–83° C.

EXAMPLE 4

N-1-methanesulfonylspiro(3H-indole-3,4'-piperidin)-1-yl]-3-benzyloxy-2-(2-methoxybenzylamino) propionamide hydrochloride To the product of Description 2 (0.48 g, 1 mmol), in dry dimethylformamide (1 ml), was added 2-methoxybenzaldehyde (0.11 g, 1.1 mmol), followed by sodium cyanoborohydride (0.09 g, 2 mmol), and the mixture stirred at room temperature for 16 hours. The reaction was diluted with ethyl acetate (20 ml), and washed with water (5×10 ml), dried over magnesium sulfate, filtered, and the solvent evaporated at reduced pressure. The residue was purified by chromatography on silica gel, (eluent 1% methanol/dichloromethane), to afford the title compound. Found: C, 61.84; H, 6.43; N, 6.68. $C_{31}H_{37}N_3O_5S.HCl.0.25 (H_2O)$ requires: C, 61.58; H, 6.42; N, 6.95%. m/e (CI$^+$) 564 (MH$^+$).

By the method of Example 2, or Example 4, the following compounds were prepared from the known aldehydes.

EXAMPLE 5

N-[1-methanesulfonylspiro(3H-indole-3,4'-piperidin)-1-yl]-2-(benzylamino)-3-benzyloxypronionamide, hydrochloride Found: C, 61.47; H, 6.31; N, 7.62. $C_{30}H_{35}N_3O_4S.HCl.H_2O$ requires: C, 61.47; H, 6.31; N, 7.62%.

EXAMPLE 6

N[1-methanesulfonylspiro(3H-indole-3,4'-piperidin)-1-yl]-3-benzyloxy-2-(2-chlorobenzylamino) propionamide hydrochloride Found: C, 58.90; H, 5.80; N, 6.69. $C_{30}H_{34}N_3O_4SCl.HCl.0.25(H_2O)$ requires: C, 59.16; H, 5.88; N, 6.90%. m/e (CI$^+$) 568 (MH$^+$)

EXAMPLE 7

N-[1-methanesulfonylspiro(3H-indole-3,4'-piperidin)-1-yl]-3-benzyloxy-2-(3-chorobenzylamino) propionamide hydrochloride Found: C, 58.23; H, 5.78; N, 6.63. $C_{30}H_{34}N_3O_4SCl.HCl.H_2O$ requires: C, 57.87; H, 5.99; N,6.74%. m/e (CI$^+$) 568 (MH$^+$).

EXAMPLE 8

N-[1-methanesulfonylsoiro(3H-indole-3,4'-piperidin)-1-yl]-3-benzyloxy-2-(4-chlorobenzylamino) propionamide hydrochloride Found: C, 58.59; H, 5.93; N, 6.76. $C_{30}H_{34}N_3O_4SCl.HCl.0.5(H_2O)$ requires: C, 58.72; H, 5.91; N, 6.85%. m/e (CI$^+$) 568 (MH$^+$).

EXAMPLE 9

N-[1-methanesulfonylspiro(3H-indole-3,4'-piperidin)-1-yl]-3-benzyloxy-2-(3-bromobenzylamino) propionamide hydrochloride Found: C, 54.08; H, 5.57; N, 6.16. $C_{30}H_{34}N_3O_4SBrHCl.H_2O$ requires: C, 54.01; H, 5.59; N, 6.29%. m/e (CI$^+$) 614 (MH$^+$).

EXAMPLE 10

N-[1-methanesulfonylspiro(3H-indole-3,4'-piperidine)-1-yl]-3-benzyloxy-2-(3-fluorobenzylamino)propionamide, hydrochloride Found: C, 60.24; H, 5.94; N, 6.76. $C_{30}H_{34}N_3O_4SF.HCl.0.5(H_2O)$ requires: C, 60.34; H, 6.08; N, 7.04%. m/e (CI$^+$) 552 (MH$^+$).

EXAMPLE 11

N-[1-methanesulfonylspiro(3H-indole-3,4'-piperidin)-1-yl]-3-benzyloxy-2-(3-cyanobenzylamino) propionamide hydrochloride Found: C, 60.42; H, 5.78; N, 8.81. $C_{30}H_{34}N_4O_4S.HCl.H_2O$ requires: C, 60.72; H, 6.08; N, 9.13%. m/e (CI$^+$) 559 (MH$^+$).

EXAMPLE 12

N-[1-methanesulfonylspiro(3H-indole-3,4'-piperidin)-1-yl]-3-benzyloxy-2-(3-nitrobenzylamino)propionamide hydrochloride Found: C, 56.99; H, 5.64; N, 8.64. $C_{30}H_{34}N_4O_6S.HCl.H_2O$ requires: C, 56.91; H, 5.84; N, 8.85%. m/e (Cl$^+$) 579 (MH$^+$).

EXAMPLE 13

N-[1-methanesulfonylspiro(3H-indole-3,4'-piperidin)-1-yl]-3-benzyloxy-2-(3-methylbenzylamino)propionamide hydrochloride Found: C, 61.79; H, 6.64; N, 6.83. $C_{34}H_{37}N_3O_4S.HCl.H_2O$ requires: C, 61.83; H, 6.69; N, 6.97%. m/e (Cl$^+$) 548 (MH$^+$).

EXAMPLE 14

N-[1-methanesulfonylspiro(3H-indole-3,4'-piperidin)-1-yl]-3-benzyloxy-2-(3-methoxybenzyl-amino)propionamide, hydrochloride Found: C, 60.06; H, 6.32; N, 6.41. $C_{31}H_{37}N_3O_5S.HCl.H_2O$ requires: C, 60.23; H, 6.52; N, 6.79%. m/e (Cl$^+$) 564 (MH$^+$).

EXAMPLE 15

N-[1-methanesulfonylspiro(3H-indole-3,4'-piperidin)-1-yl]-3-benzyloxy-2-(4-methoxybenzyl-amino)pronionamide, hydrochloride Found: C, 58.89; H, 6.40; N, 6.94. $C_{31}H_{37}N_3O_5S.HCl.2(H_2O)$ requires: C, 58.53; H, 6.65; N, 6.61%. m/e (Cl$^+$) 564 (MH$^+$).

EXAMPLE 16

N-[1-methanesulfonylspiro(3H-indole-3,4'-piperidin)-1-yl]-3-benzyloxy-2-(4-(dimethylamino)-benzylamino)propionamide hydrochloride Found: C, 57.67; H, 6.42; N, 7.96. $C_{32}H_{40}N_4O_4S.2(HCl).(H_2O)$ requires: C, 57.56; H, 6.64; N, 8.39%. m/e (Cl$^+$) 577 (MH$^+$).

EXAMPLE 17

N-[1-methanesulfonylspiro(3H-indole-3,4'-piperidin)-1-yl]-3-benzyloxy-2-(2,4-dichlorobenzyl-amino)propionamide hydrochloride Found: C, 55.20; H, 5.58; N, 6.14. $C_{30}H_{33}N_3O_4SCl_2.HCl.0.5(H_2O)$ requires: C, 55.60; H, 5.44; N, 6.48%. m/e (Cl$^+$) 602 (MH$^+$).

EXAMPLE 18

N-[1-methanesulfonylspiro(3H-indole-3,4'-piperidin)-1-yl]-3-benzyloxy-2-(3,5-dichlorobenzyl-amino)propionamide hydrochloride Found: C, 54.96; H, 5.47; N, 6.45. $C_{30}H_{33}N_3O_4SCl_2.HCl.H_2O$ requires: C, 54.84; H, 5.53; N, 6.40%. m/e (Cl$^+$) 602 (MH$^+$).

EXAMPLE 19

N-[1-methanesulfonylspiro(3H-indole-3,4'-piperidin)-1-yl]-3-benzyloxy-2-(2,3-dichlorobenzyl-amino)propionamide hydrochloride Found: C, 54.48; H, 5.13; N, 6.36. $C_{30}H_{33}N_3O_4SCl_2.HCl.H_2O$ requires: C, 54.84; H, 5.53; N, 6.40%. m/e (Cl$^+$) 602 (MH$^+$).

EXAMPLE 20

N-[1-methanesulfonylspiro(3H-indole-3,4'-piperidin)-1-yl]-3-benzyloxy-2-(2,6-dichlorobenzyl-amino)propionamide hydrochloride m/e (Cl$^+$) 602 (MH$^+$).

EXAMPLE 21

N-[1-methanesulfonylspiro(3H-indole-3,4'-piperidin)-1-yl]-3-benzyloxy-2-(3,5-dimethoxybenzyl-amino)propionamide hydrochloride Found: C, 59.83; H, 6.40; N, 6.62. $C_{32}H_{39}N_3O_6S.HCl.0.5(H_2O)$ requires: C, 60.13; H, 6.47; N, 6.57%. m/e (Cl$^+$) 594 (MH$^+$).

EXAMPLE 22

N-[1-methanesulfonylspiro(3H-indole-3,4'-piperidin)-1-yl]-3-benzyloxy-2-(3-chloro-5-methoxybenzylamino)propionamide hydrochloride Found: C, 57.22; H. 5.88; N, 6.35. $C_{33}H_{36}N_3O_5SCl.HCl.H_2O$ requires: C, 56.96; H, 6.16; N, 6.42%. m/e (Cl$^+$) 598 (MH$^+$).

EXAMPLE 23

N-[1-methanesulfonylspiro(3H-indole-3,4'-piperidin)-1-yl]-3-benzyloxy-2-(3,4-dimethoxybenzyl-amino)propionamide, hydrochloride Found: C, 60.12; H, 6.68; N, 6.52. $C_{32}H_{39}N_3O_6S.HCl.0.5(H_2O)$ requires: C, 60.13; H, 6.47; N, 6.57%. m/e (Cl$^+$) 594 (MH$^+$).

EXAMPLE 24

N-[1-methanesulfonylspiro(3H-indole-3,4'-piperidin)-1-yl]-3-benzyloxy-2-(3,4-methylenedioxybenzylamino)propionamide hydrochloride Found: C, 59.98; H, 6.01; N, 6.64. $C_{31}H_{35}N_3O_6S.HCl.0.25(H_2O)$ requires: C, 60.18; H, 5.95; N, 6.79%. m/e (Cl$^+$) 578 (MH$^+$).

EXAMPLE 25

N-[1-methanesulfonylspiro(3H-indole-3,4'-piperidin)-1-yl]-3-benzyloxy-2-(1-naphthylmethylamino)propionamide, hydrochloride Found: C, 64.71; H, 6.25; N, 6.58. $C_{34}H_{37}N_3O_4S.HCl.0.5(H_2O)$ requires: C, -64.90; H, 6.24; N, 6.67%. m/e (Cl$^+$) 584 (MH$^+$).

EXAMPLE 26

N-[1-methanesulfonylspiro(3H-indole-3,4'-piperidin)-1-yl]-3-benzyloxy-2-(2-naphthylmethylamino)propionamide hydrochloride Found: C, 63.72; H, 5.99; N, 6.51. $C_{34}H_{37}N_3O_4S.HCl.H_2O$ requires: C, 63.98; H, 6.31; N, 6.58%. m/e (Cl$^+$) 584 (MH$^+$).

EXAMPLE 27

N-[1-methanesulfonylspiro(3H-indole-3,4'-piperidin)-1-yl]-3-benzyloxy-2-(2-pyridylmethylamino)propionamide dihydrochloride Found: C, 56.88; H, 6.22; N, 9.42. $C_{29}H_{34}N_4O_4S.2(HCl).0.5(H_2O)$ requires: C, 56.91; H, 6.01; N, 9.15%. m/e (Cl$^+$) 535 (NM$^+$). mp =98° C.

EXAMPLE 28

N-[1-methanesulfonylspiro(3H-indole-3,4'-piperidin)-1-yl]-3-benzyloxy-2-(3-pyridylmethylamino)propionamide dihydrochloride m/e (Cl$^+$) 535 (MH$^+$). mp=156°–158° C.

EXAMPLE 29

N-[1-methanesulfonylspiro(3H-indole-3,4'-piperidin)-1-yl]-3-benzyloxy-2-(4-pyridylmethylamino)pronionamide dihydrochloride m/e (Cl$^+$) 535 (MH$^+$). mp=135°–137° C.

EXAMPLE 30

N-[1-methanesulfonylspiro(3H-indole-3,4'-piperidin) -1-yl]-3-benzyloxy-2-(2-furylmethylamino)propionamide dihydrochloride m/e (Cl$^+$) 524 (MH$^+$). mp=112° C.

EXAMPLE 31

N-[1-methanesulfonylspiro(3H-indole-3,4'-piperidin)-1-yl]-3-benzyloxy-2-[(5-methylfur-2-yl)methylamino]propionamide hydrochloride Found: C, 58.66; H, 6.78; N, 7.29. $C_{29}H_{35}N_3O_5S$. $HCl.H_2O$ requires: C, 58.82; H, 6.47; N, 7.09%. m/e (Cl$^+$) 537 (MH$^+$).

EXAMPLE 32

N-[1-methanesulfonylspiro(3H-indole-3,4'-piperidin)-1-yl]-3-benzyloxy-2-[(3-methylthiophen-2-yl)methylamino]propionamide hydrochloride Found: C, 57.85; H, 6.30; N, 6.64. $C_{29}H_{35}N_3O_4S2.HCl.1.5(H_2O)$ requires: C, 57.79; H, 6.10; N, 6.97%. m/e (Cl$^+$) 554 (MH$^+$).

EXAMPLE 33

N-[1-methanesulfonylspiro(3H-indole-3,4'-piperidin)-1-yl]-3-benzyloxy-2-[(5-methylthiophen-2-yl)methylamino]propionamide hydrochloride Found: C, 55.70; H, 6.15; N, 6.40. $C_{29}H_{35}N_3O_4S_2.HCl.2(H_2O)$ requires: C, 55.62; H, 6.43; N, 6.71%. m/e (Cl$^+$) 554 (MH$^+$).

EXAMPLE 34

N-[1-methanesulfonylspiro(3H-indole-3,4'-piperidin)-1l-yl]3-benzyloxy-2-(N-(3,4-dichlorobenzyl)-N-(methyl)amino)propionamide hydrochloride To the product of Example 2 (113 mg, 0. 188 mmol), suspended in dry dimethylformamide (2 ml), was added sodium cyanoborohydride (44 mg), paraformaldehyde (100 mg), and the mixture was stirred at room temperature for 16 hours. The reaction was diluted with ethyl acetate (20 ml), and washed with water (5×10 ml), dried over magnesium sulfate, filtered, and the solvent evaporated at reduced pressure. The residue was purified by chromatography on silica gel, (eluent 2.5% methanol/dichloromethane), to afford the title compound. Found: C, 56.05; H, 5.77; N, 6.35. $C_{31}H_{35}N_3O_4SCl_2.HCl.0.5(H_2O)$ requires: C, 56.24; H, 5.63; 6.35%. m/e (Cl$^+$) 616 (MH$^+$).

By the method of Example 1 the following compounds were prepared from the known acid chlorides and the product of Description 2:

EXAMPLE 35

N-[1-methanesulfonylspiro(3H-indole-3,4'-piperidin)-1-yl]-3-benzyloxy-2-(2-chlorobenzamido)propionamide Found: C, 62.27; H,, 5.79; N, 6.91. $C_{30}H_{32}N_3O_5SCl$ requires: C, 61.90; H, 5.54; N, 7.22%. m/e (Cl$^+$) 582 (MH$^+$).

EXAMPLE 36

N-[1-methanesulfonylspiro(3H-indole-3,4'-piperidin)-1-yl]-3-benzyloxy-2-(3-chlorobenzamido)pronionamide Found: C, 61.78; H, 5.54; N, 6.96. $C_{30}H_{32}N_3O_5SCl$ requires: C, 61.90; H, 5.54; N, 7.22%. m/e (Cl$^+$) 582 (MH$^+$).

EXAMPLE 37

N-[1-methanesulfonylspiro(3H-indole-3,4'-piperidin)-1-yl]-3-benzyloxy-2-(4-chlorobenzamido)propionamide Found: C, 61.10; H, 5.49; N, 6.86. $C_{30}H_{32}N_3O_5SCl.0.5(H_2O)$ requires: C, 60.95; H, 5.63; N, 7.11%. m/e (Cl$^+$) 582 (MH$^+$).

EXAMPLE 38

N-[1-methanesulfonylspiro(3H-indole-3,4'-piperidin)-1-yl]-3-benzyloxy-2-(2,6-dichlorobenzamido)propionamide Found: C, 56.51; H, 4.80; N, 6.34. $C_{30}H_{31}N_3O_5SCl_2.H_2O$ requires: C, 56.78; H, 5.24; N, 6.62%. m/e (Cl$^+$) 616 (MH$^+$).

EXAMPLE 39

N-[1-methanesulfonylspiro(3H-indole-3,4'-piperidin)-1-yl]-3-benzyloxy-2-(3,5-dichlorobenzamido)pronionamide Found: C, 58.34; H, 4.73; N, 6.64. $C_{30}H_{31}N_3O_5SCl_2$ requires: C, 58.44; H, 5.06; N, 6.81%. m/e (Cl$^+$) 616 (MH$^+$).

EXAMPLE 40

N-[1-methanesulfonylspiro(3H-indole-3,4'-piperidin)-1-yl]-3-benzyloxy-2-(2,5-dichlorobenzamido)propionamide Found: C, 56.80; H, 4.94; N, 6.53. $C_{30}H_{31}N_3O_5SCl_2.H_2O$ requires: C. 56.78 H, 5.24; N, 6.62%. m/e (Cl$^+$) 616 (MH$^+$).

EXAMPLE 41

N-[1-methanesulfonylspiro(3H-indole-3,4'-piperidin)-1-yl]-3-benzyloxy-2-(2,4-dichlorobenzamido)propionamide Found: C, 57.67; H, 4.86; N, 6.30. $C_{30}H_{32}N_3O_5SCl_2.0.6(H_2O)$ requires: C, 57.43; H, 5.17; N, 6.70%. m/e (Cl$^+$) 616 (MH$^+$).

EXAMPLE 42

N-[1-methanesulfonylspiro(3H-indole-3,4'-piperidin)-1-yl]-3-benzyloxy-2-(2,3-dichlorobenzamido)propionamide Found: C, 58.22; H, 4.86; N, 6.69. $C_{30}H_{31}N_3O_5SCl_2$ requires: C, 58.44; H, 5.06; N, 6.81%. m/e (Cl$^+$) 616 (MH$^+$).

EXAMPLE 43

N-[1-methanesulfonylspiro(3H-indole-3,4'-piperidin)-1-yl]-3-benzyloxy-2-(3,4-dimethoxybenzamido)propionamide Found: C, 59.50; H, 6.17; N, 6.35. $C_{32}H_{37}N_3O_7S.2(H_2O)$ requires: C, 59.70 H, 6.42; N, 6.53%. m/e (Cl$^+$) 608 (MH$^+$).

EXAMPLE 44

N-[1-methanesulfonylspiro(3H-indole-3,4'-piperidin)-1-yl]-3-benzyloxy-2-benzamidopropionamide Found: C, 65.69; H, 5.84 N, 7.56. $C_{30}H_{33}N_3O_5S$ requires: C, 65.79; H, 6.07; N, 7.67%. m/e (Cl$^+$) 547 (MH$^+$).mp= 78°–81° C.

EXAMPLE 45

N-[1-methanesulfonylspiro(3H-indole-3,4'-piperidin)-1-yl]-3-benzyloxy-2-(3-(2-propyloxy)benzamido) propionamide Found: C, 64.42; H, 6.20; N, 6.76. $C_{33}H_{39}N_3O_6S$ requires: C, 64.47; H, 6.56; N, 6.83%. m/e (Cl$^+$) 606 (MH$^+$).

EXAMPLE 46

N-[1-methanesulfonylspiro(3H-indole-3,4'-piperidin)-1-yl]-3-benzyloxy-2-[(1-naphthyl)carboxamido]propionamide m/e (Cl$^+$) 598 (MH$^+$).mp=76°–79° C.

EXAMPLE 47

N-[1-methanesulfonylspiro(3H-indole-3,4'-piperidin)-1-yl]-3-benzyloxy-2-[(2-naphthyl)carboxamido]propionamide m/e (Cl$^+$) 598 (MH$^+$).mp=86°–89° C.

EXAMPLE 48

N-[1-methanesulfonylspiro(3H-indole-3,4'-piperidin)-1-yl]-3-benzyloxy-2-(phenylacetamido)propionamide Found: C, 65.37; H, 6.03; N, 7.17. $C_{31}H_{35}N_3O_5S.0.5(H_2O)$ requires: C, 65.24; H, 6.34; N, 7.36%. m/e (Cl$^+$) 562 (MH$^+$).

EXAMPLE 49

N-[1-methanesulfonylspiro(3H-indole-3,4'-piperidin)-1-yl]-3-benzyloxy-2-((3,4-dichlorophenyl)acetamido)propionamide Found: C, 58.22; H, 5.19; N, 6.28. $C_{31}H_{33}N_3O_5SCl_2.0.5(H_2O)$ requires: C, 58.21; H, 5.35; N, 6.57%. m/e (Cl$^+$) 630 (MH$^+$).

EXAMPLE 50

N-[1-methanesulfonylspiro(3H-indole-3,4'-piperidin)-1-yl]-3-benzyloxy-2-[(3,5-bis(trifluoromethyl)phenyl)acetamido]propionamide Found: C, 56.86 H. 4.69: N. 5.92. $C_{33}H_{33}N_3O_5SF_6$ requires: C, 56.81; H, 4.77; N, 6.02%. m/e (Cl$^+$) 698 (MH$^+$).

EXAMPLE 51

N-[1-methanesulfonylspiro(3H-indole-3,4'-piperidin)-1-yl]-3-benzyloxy-2-(diphenylacetamido)propionamide Found: C, 69.10; H, 6.29; N, 6.25. $C_{37}H_{39}N_3O_5S.0.3(H_2O)$ requires: C, 69.09; H, 6.21; N, 6.53%. m/e (Cl$^+$) 638 (MH$^+$).

By the method of Example 3 the following compounds were prepared from the known acids and the product of Description 2:

EXAMPLE 52

N-[1-methanesulfonylspiro(3H-indole-3,4'-piperidin)-1-yl]-3-benzyloxy-2-(4-pyridylcarboxamido)propionamide m/e (Cl$^+$) 549 (MH$^+$). mp=126°–128° C.

EXAMPLE 53

N-[1-methanesulfonylspiro(3H-indole-3,4'-piperidin)-1-yl]-3-benzyloxy-2-(2-pyridylcarboxamido)propionamidehydrochloride m/e (Cl$^+$) 549 (MH$^+$). mp=95°–98° C.

EXAMPLE 54

N-[1-methanesulfonylspiro(3H-indole-3,4'-piperidin)-1-yl]-3-benzyloxy-2-(8-quinolinylcarboxamido)propionamidehydrochloride m/e (Cl$^+$) 599 (MH$^+$). mp=80°–83° C.

N-tert-butoxycarbonylserine was treated with sodium hydride and the appropriate substituted benzyl chlorides or bromides according to the method of Sugano. H, and Miyoshi. M, *J. Org. Chem*, 41, 2352, (1976), to afford the corresponding N-tert-butoxycarbonyl-O-benzyl-serine after ester saponification. The following compounds were prepared from the N-tert-butoxycarbonyl-O-benzyl-serines according to the method of Descriptions 1 or 2, and Examples 1 or 2:

EXAMPLE 55

N-[1-methanesulfonylspiro(3H-indole-3,4'-piperidin)-1-yl]-2-(benzylamino)-3-(2-chlorobenzyloxy)propionamide hydrochloride Found: C, 57.83; H, 5.85; N, 6.30. $C_{30}H_{32}N_3O_4SCl.HCl.1.25(H_2O)$ requires: C, 57.64; H, 5.72; N, 6.72%. m/e (Cl$^+$) 568 (MH$^+$).

EXAMPLE 56

N-[1-methanesulfonylspiro(3H-indole-3,4'-piperidin)-1-yl]-2-(1)benzylamino)-3-(3-chlorobenzyloxy)propionamidehydrochloride Found: C, 56.73; H, 5.89; N, 6.51. $C_{30}H_{32}N_3O_4SCl.HCl.2(H_2O)$ requires: C, 56.42; H, 5.84; N, 6.58%. m/e (Cl$^+$) 568 (MH$^+$).

EXAMPLE 57

N-[1-methanesulfonylspiro(3H-indole-3,4'-piperidin)-1-yl]-2-(benzylamino)-3-(4-chlorobenzyloxy)propionamide hydrochloride Found: C, 58.32; H, 5.81; N, 6.56. $C_{30}H_{32}N_3O_4SCl.HCl.H_2O$ requires: C, 58.06; H, 5.68; N, 6.77%. m/e (Cl$^+$) 568 (MH$^+$).

EXAMPLE 58

N-[1-methanesulfonylspiro(3H-indole-3,4'-piperidin)-1-yl]-3-(2-chlorobenzyloxy)-2-(3,4-dichlorobenzylamino)propionamide hydrochloride Found: C, 52.74; H, 4.90; N, 5.96. $C_{30}H_{32}N_3O_4SCl_3.HCl.0.5(H_2O)$ requires: C, 52.79; H, 5.02; N, 6.18%. m/e (Cl$^+$) 636 (MH$^+$).

EXAMPLE 59

N-[1-methanesulfonylspiro(3H-indole-3,4'-piperidin)-1-yl]-3-(3-chlorobenzyloxy)-2-(3,4-dichlorobenzylamino)propionamide hydrochloride Found: C, 52.33; H, 5.01; N, 5.75. $C_{30}H_{32}N_3O_4SCl_3.HCl.H_2O$ requires: C, 52.10; H, 5.10; N, 6.07%. m/e (CI$^+$) 636 (MH$^+$).

EXAMPLE 60

N-[1-methanesulfonylspiro(3H-indole-3,4'-piperidin)-1yl-]-3-(4-chlorobenzyloxy)-2-(3,4-dichlorobenzylamino)propionamide hydrochloride Found: C, 52.36; H, 4.77; N, 6.07. $C_{30}H_{32}N_3O_4SCl_3.HCl.0.5(H_2O)$ requires: C, 52.22; H, 4.89; N, 6.09%. m/e (CI$^+$) 636 (MH$^+$).

EXAMPLE 61

N-[1-methanesulfonylspiro(3H-indole-3,4'-piperidin)-1-yl]-3-[3,5-bis(trifluoromethyl)benzyloxy-2-(3,5-dichlorobenzamido)-propionamide Found: C, 50.99; H, 3.77; N, 5.60. $C_{32}H_{29}N_3O_5SCl_2F_6$ requires: C, 51.07; H 3.88; N, 5.58%. m/e (CI$^+$) 752 (MH$^+$).

The following compound was prepared from N-tert-butoxylcarbonyl-S-benzyl-cysteine according to the method of Descriptions 1 and 2, and Example 2

EXAMPLE 62

N-[1-methanesulfonylspiro(3H-indole-3,4'-piperidin)-1-yl]-3-(benzylthio)-2-(3,4-dichlorobenzylamino)pronionamide, hydrochloride Found: C, 54.63; H, 5.11; N, 6.19. $C_{30}H_{33}N_3O_3S_2.HCl$ requires: C, 55.00; H, 5.23; N, 6.41%. m/e (CI$^+$) 618 (MH$^+$). m.p. 215°–217° C.

N-tert-Butoxycarbonylserine was treated with sodium hydride and the appropriate substituted benzyl or naphthyl-methyl chlorides or bromides according to the method of Sugano, H. and Miyoshi, M.,*J. Org. Chem.*, 41, 2352 (1976) to give, after ester saponification, the corresponding O-substituted N-tert-butoxycarbonylserine. The following compounds were prepared from the O-substituted N-tert-butoxycarbonylserines according to the method of Descriptions 1 or 2, and Examples 1 or 2:

EXAMPLE 63

N-[1-Methanesulfonylspiro(3H-indole-3,4'-piperidin)-1-yl]-2-(benzylamino)-3-[naphth-2-yl)methoxy]propionamide, hydrochloride Found: C, 64.64; H, 6.27; N, 6.34. $C_{34}H_{37}N_3O_4S.HCl.0.5H_2O$ requires: C, 64.90; H, 6.25; N, 6.68%. m/e (CI$^+$) 584 (MH$^+$).

EXAMPLE 64

N-[1-Methanesulfonylspiro(3H-indole-3,4'-piperidin)-1-yl]-2-(benzylamino)-3-[(naphth-1-yl)methoxy]propionamide, hydrochloride Found: C, 63.64; H, 6.28; N, 6.59. $C_{34}H_{37}N_3O_4S.HCl.H_2O$ requires: C, 63.99; H, 6.32; N, 6.58%. m/e (CI$^+$) 584 (MH$^+$).

EXAMPLE 65

N-[1-Methanesulfonylspiro(3H-indole-3,4'-piperidin)-1-yl]-2-(benzylamino)-3-(3,4-dichlorobenzyloxy)propionamide, hydrochloride Found: C, 55.53; H, 5.33; N, 6.85. $C_{30}H_{33}Cl_2N_3O_4S.HCl.0.5H_2O$ requires: C, 55.60; H, 5.44; N, 6.48%. m/e (CI$^+$) 602 (MH$^+$).

EXAMPLE 66

N-[1-Methanesulfonylspiro(3H-indole-3,4'-piperidin)-1-yl]-2-(3,4-dichlorobenzylamino)-3-(3,4-dichlorobenzyloxyy)propionamide, hydrochloride Found: C, 49.64; H, 4.42; N, 5.47. $C_{30}H_{31}Cl_4N_3O_4S.HCl.H_2O$ requires: C, 49.64; H, 4.72; N, 5.79%. m/e (CI$^+$) 670 (MH$^+$).

EXAMPLE 67

N-[1-Methanesulfonylspiro(3H-indole-3,4'-piperidin)-1-yl]-2-]N-(methyl)benzylamino]-3-(3,4-dichlorobenzyloxy)propionamide, hydrochloride Methyl iodide (0.1 ml) was added to a mixture of N-[1-methanesulfonylspiro(3H-indole-3,4'-piperidin)-1-yl]-2-(benzylamino)-3-(3,4-dichlorobenzyloxy)propionamide hydrochloride (48 mg) and potassium carbonate (100 mg) in dichloromethane/DMF (1:1, 4 ml) and the mixture was stirred at room temperature for 16 hours. The mixture was diluted with ether, washed with water (3×), dried ($Na_2SO_4$) and the solvent was evaporated under reduced pressure. The residue was purified by column chromatography on silica gel, eluting with ethyl acetate/hexane (3:1). The residue was dissolved in ethanolic hydrogen chloride and the solvent was evaporated under reduced pressure. The residue was triturated with ether and the solid was collected and dried in vacuo to afford the title compound as a colourless solid. Found: C, 55.28; H, 5.68; N, 6.11. $C_{31}H_{35}Cl_2N_3O_4S.HCl.H_2O$ requires: C, 55.48; H, 5.71; N, 6.26%. m/e (CI$^+$) 616 (M$^+$).

EXAMPLE 68

N-[1-Methanesulfonylspiro(3H-indole-3,4'-piperidin)-1-yl]-3-(3,4-dichlorobenzyloxy)-2-(dimethyl)aminopronionamide, hydrochloride a) N-[1-Methanesulfonylspiro(3H-indole-3,4'-piperidin)-1-yl]-2-amino-3-(3,4-dichlorobenzyloxy)propionamide N-tert-Butoxycarbonylserine was treated with sodium hydride and 3,4-dichlorobenzyl bromide according to the method of Sugano, H. and Miyoshi, M.,*J. Org. Chem.*, 41, 2352 (1976) to give, after ester saponification, N-tert-butoxycarbonyl-O-(3,4-dichlorobenzyl)serine. This was then coupled according to the method of Description 1 and deprotected according to the method of Description 2 to give the title compound. m/e (CI$^+$) 512 (MH$^+$).

b) N-[1-Methanesulfonylspiro(3H-indole-3,4'-piperidin)-1-yl]-3-(3,4-dichlorobenzyloxy)-2-(dimethyl)aminopropionamide, hydrochloride Aqueous formaldehyde (38%, 1 ml) and sodium cyanoborohydride (35 mg) were added to a solution of the product of step (a) (240 mg) in acetonitrile (20 ml). Acetic acid was added until the reaction pH was 5 and the mixture was stirred at room temperature for 4 hours. The solvent was evaporated under reduced pressure and the residue was partitioned between ethyl acetate and aqueous sodium hydroxide (1M). The organic layer was dried ($MgSO_4$) and the solvent was evaporated under reduced pressure. The residue was purified by column chromatography on silica gel, eluting with dichloromethane/methanol (98:2). The residue was dissolved in ethanolic hydrogen chloride (5M, 3 ml) and the solvent was evaporated under reduced pressure. The solid was recrystallized from isopropyl alcohol/ether to afford the title compound as a colourless solid (165 mg, 61%). Found: C, 51.14; H, 5.70; N, 7.06. $C_{25}H_{31}Cl_2N_3O_4S.HCl.0.5H_2O$ requires: C, 51.24; H, 5.68; N, 7.17%. m/e (CI$^+$) 540 (MN$^+$).

EXAMPLE 69

N-[1-Methanesulfonylspiro(3H-indole-3,4'-piperidin)-1-yl]-3-(3,4-dichlorobenzylthio)-2-(benzylamino)propionamide, hydrochloride 3,4-Dichlorobenzylmercaptan (0.3 ml, 1.6 mmol) was added dropwise to a stirred, cooled (0° C.) suspension of sodium hydride (64 mg, 1.6 mmol) in DMF (5 ml) and the mixture was stirred at 0° C. for 1 hour. N-Benzyl-N-(benzyloxycarbonyl)serine-β-lactone [prepared according to Vederas, J. C., et. al., *J. Am. Chem. Soc.*, 109, 4649 (1987), 0.40 g, 1.2 mmol] in DMF (5 ml) was added and the mixture was warmed to 25° C. and stirred for 2 hours [*J. Am. Chem. Soc.*, 107, 7105 (1985)]. Ethyl acetate (50 ml) and water (20 ml) were added and the organic layer was washed with water (3×20 ml), dried (MgSO$_4$) and the solvent was evaporated under reduced pressure. The residue was dissolved in dichloromethane (10 ml) and 1-methanesulfonylspiro(3H-indole-3,4'-piperidine) hydrochloride (0.282 g, 1.06 mmol), triethylamine (0.31 ml, 2.2 mmol) and bis(2-oxo-3-oxazolidinyl) phosphinic chloride (0.27 g, 1.06 mmol) were added The mixture was stirred at room temperature for 2 hours, then ethyl acetate (50 ml) and water (20 ml) were added. The organic layer was separated, dried (MgSO$_4$) and the solvent was evaporated under reduced pressure. The residue was purified by column chromatography on silica eluting with ethyl acetate/hexane (30:70) to give N-[1-methanesulfonylspiro(3H-indole-3,4'-piperidin)-1-yl]-3-(3,4-dichlorobenzylthio)-2-[N-(benzyl)-benzyloxycarbonylamino]propionamide as a colourless oil (0.80 g). A sample (0.10 g) was dissolved in dichloromethane (3 ml), cooled to −10° C. and boron tribromide (1.0M in CH$_2$Cl$_2$, 0.7 ml) was added. The mixture was warmed to 25° C. for 20 minutes, aqueous sodium hydroxide (4M, 5 ml) was added and the mixture was extracted with ethyl acetate (20 ml). The organic layer was dried (MgSO$_4$) and the solvent was evaporated under reduced pressure. The residue was treated with ethereal hydrogen chloride and the solid was collected and dried in vacuo to give the title compound as a colorless solid. NMR δ$_H$ (360 MHz, DMSO-d$_6$) 7.21–7.48 (10H, m), 7.03 (1H, m), 6.97 (1H, m), 4.05–4.21 (4H, m), 3.84–3.96 (2H, 3.64–3.73 (2H, m), 3.22 (1H, m), 2.99 (3H, s), 2.64–2.97 (4H, m), 1.67 (2H, m), 1.53 (2H, m). m/e (CI$^+$) 618 (MH$^+$).

EXAMPLE 70

N-[1-Methanesulfonylspiro(3H-indole-3,4'-piperidin)-1-yl]-3-(3,4-dichlorobenzylsulfonyl)-2-(benzylamino)propionamide, hydrochloride m-Chloroperoxybenzoic acid (2.6 g, 8.8 mmol) was added to N-[1-methanesulfonylspiro(3H-indole-3,4'-piperidin)-1-yl]-3-(3,4-dichlorobenzylthio)-2-[N-(benzyl)benzyloxycarbonylamino]propionamide (0.228 g, 0.3 mmol) in dichloromethane (2 ml) and the mixture was stirred at room temperature for 16 hours. The mixture was diluted with dichloromethane (30 ml) and washed with aqueous sodium bisulfite (15 ml), aqueous sodium carbonate (15 ml) and brine (15 ml). The organic layer was dried (MgSO$_4$) and the solvent was evaporated under reduced pressure. The residue was dissolved in dichloromethane (1 ml), cooled to −10° C. and boron tribromide (1.0M in CH$_2$Cl$_2$, 0.7 ml) was added. The mixture was warmed to 25° C. for 20 minutes, aqueous sodium hydroxide (4M, 5 ml) was added and the mixture was extracted with ethyl acetate (20 ml). The organic layer was dried (MgSO$_4$) and the solvent was evaporated under reduced pressure. The residue was treated with ethereal hydrogen chloride and the solid was collected and dried in vacuo to give the title compound as a colorless solid. NMR δ$_H$ (360 MHz, DMSO-d$_6$) 7.73 (2H, m), 7.46 (7H, m), 7.24–7.34 (2H, m), 7.09 (1H, m), 4.86 (1H, m), 4.78 (2H, s), 4.41 (1H, m), 4.04 (3H, m), 3.94 (2H, s), 3.81 (1H, m), 3.70 (1H, m), 3.24 (1H, m), 3.06 (3H, s), 2.85 (1H, m), 1.75 (4H, m). m/e (CI$^+$) 650 (MH$^+$).

EXAMPLE 71

N-[1-Methanesulfonylspiro(3H-indole-3,4'-piperidin)-1-yl]-2,3-bis(benzylamino)propionamide, hydrochloride N-bis(trimethylsilyl)amine (0.11 ml, 0.543 mmol) was added to a solution of N-benzyl-N-benzyloxycarbonyl)serine-β-lactone [prepared according to Vederas, J. C., et. al., *J. Am. Chem. Soc.*, 109, 4649 (1987), 0.13 g, 0.418 mmol] in acetonitrile (2 ml) and the mixture was stirred at room temperature for 16 hours [Vederas, J. C. et. al. *Tetrahedron Lett.*, 35, 7605 (1994)]. The mixture was cooled to 0° C. and aqueous hydrochloric acid (1M, 2 ml) was added. The solvent was evaporated under reduced pressure and the residue was filtered. The filtrate was treated with aqueous sodium hydroxide (2M) until the pH was greater than 10 and di-tert-butyldicarbonate (200 mg) was added. The mixture was stirred at room temperature for 12 hours, then ethyl acetate (50 ml) and water (20 ml) were added. The organic layer was separated, dried (MgSO$_4$) and the solvent was evaporated under reduced pressure. The residue was dissolved in dichloromethane (10 ml) and 1-methanesulfonylspiro(3H-indole-3,4'-piperidine) hydrochloride (0.282 g, 1.06 mmol), triethylamine (0.31 ml, 2.2 mmol) and bis(2-oxo-3-oxazolidinyl)phosphinic chloride (0.27 g, 1.06 mmol) were added. The mixture was stirred at room temperature for 2 hours, then ethyl acetate (50 ml) and water (20 ml) were added. The organic layer was separated and dried (MgSO$_4$) and the solvent was evaporated under reduced pressure. The residue was purified by column chromatography on silica eluting with ethyl acetate/hexane (30:70). The residue was dissolved in trifluoroacetic acid (2 ml) and the mixture was stirred at room temperature for 5 minutes. The solvent was evaporated under reduced pressure and the residue was dissolved in ethanol. Palladium on carbon (0.4 g) was added and the mixture was shaken under hydrogen (50 psi) for 16 hours. The mixture was filtered and the solvent was evaporated under reduced pressure. The residue was purified by column chromatography on silica eluting with CH$_2$Cl$_2$/MeOH (98:2) and the residue was treated with ethereal hydrogen chloride. The solid was collected and dried in vacuo to give the title compound as a colourless solid, m.p. 158°–160° C. m/e (CI$^+$) 533 (MH$^+$).

EXAMPLE 72

N-[1-Methanesulfonylspiro(3H-indole-3,4'-piperidin)-1-yl]-2-(benzylamino)-3-(3,4-dichlorobenzylamino)propionamide, dihydrochloride a) Methyl 2-(tert-butoxycarbonylamino)-3-(3,4-dichlorobenzylamino) propionate 3,4-Dichlorobenzylamine (880 mg) was added to a stirred solution of methyl 2-(tert-butoxycarbonylamino)acrylate (390 mg) in methanol (30 ml). The reaction mixture was warmed to reflux for 24 hours, cooled to room temperature and the solvent was evaporated under reduced pressure. The residue was purified by MPLC (70% ethyl acetate/n-hexane) to give the title compound as a clear oil (300 mg ). NMR δ$_H$ (360 MHz, CDCl₃) 1.45 (9H, s,) 2.95 (2H, d, J=3.5 Hz), 3.70 (1H, d, J=14.0 Hz), 3.75 (3H, s) 3.78 (1H, d, J=14.0 Hz), 4.41 (1H, br s) 5.34 (1H, br s), 7.12 (1H, dd, J=7.0 and 1.0 Hz), 7.37 (1H, d, J=7.0 Hz), 7.41 (1H, d, J=1.0 Hz).

b) Methyl 2-(tert-butoxycarbonylamino)-3-[N-(3,4-dichlorobenzyl) benzyloxycarbonylamino]propionate Benzylchloroformate (0.37 ml) was added in a single portion to a stirred suspension of the product of step (a) (1.0 g) in tetrahydrofuran/8% aqueous NaHCO₃ (50 ml). After 2 hours the reaction was diluted with water (50 ml) and extracted with ethyl acetate (2×50 ml). The combined organic fractions were dried (MgSO₄) and the solvent was evaporated under reduced pressure to give the title compound as a clear oil (1.09 g). NMR δ$_H$ (360 MHz, CDCl₃) 1.43 (9H, s), 3.55–3.60 (2H, m), 3.70 (3H, s), 4.48 (2H, m), 5.21 (2H, m), 5.41 (1H, br s) 5.45 (1H, br s), 6.90–7.42 (8H, m).

c) 2-(tert-Butoxycarbonylamino)-3-[N-(3,4-dichlorobenzyl) benzyloxycarbonylamino]propionic acid Lithium hydroxide (62.4 mg) was added to a solution of the product of step (b) (1.0 g) in tetrahydrofuran/water (30 ml). The resulting solution was stirred at room temperature for 4 hours, diluted with 1N HCl (50 ml) and extracted with ethyl acetate (3×50 ml). The combined organic fractions were dried (MgSO₄) and the solvent was evaporated under reduced pressure to give the title compound as a colourless foam (990 mg). NMR δ$_H$ (360 MHz, CDCl₃) 1.44 (9H, s), 3,49 (2H, m), 4.51 (3H, m), 5.17 (2H, m), 5.79 (1H, br s), 7.20–7.42 (8H, m). m/e (CI⁺) 497 (MH⁺).

d) N-[1-Methanesulfonylspiro(3H-indole-3,4'-piperidin)-1-yl]-2-amino -3-[N-(3,4-dichlorobenzyl) benzyloxycarbonylamino]propionamide Bis(2-oxo-3-oxazolidinyl)phosphinic chloride (762 mg) was added to stirred solution of the product of step (c) (990 mg), 1-methanesulfonylspiro(3H indole-3,4'-piperidine) (580 mg) and triethylamine (0.85 ml) in dichloromethane (50 ml). The resulting solution was stirred at room temperature for 18 hours, and the solvent was evaporated under reduced pressure. The residue was partitioned between ethyl acetate and water, the organic layer was separated, dried (MgSO₄) and the solvent was evaporated under reduced pressure. The recovered material was taken up in dichloromethane (20 ml) and trifluoroacetic acid (2.0 ml) was added. After 2 hours the solvent was evaporated under reduced pressure and the residue was partitioned between aqueous sodium carbonate (saturated, 20 ml) and ethyl acetate (20 ml). The organic layer was separated, dried (MgSO₄) and the solvent was evaporated under reduced pressure to give the title compound as a colourless foam (1.17 g). m/e (CI⁺) 645 (MH⁺).

e) N-[1-Methanesulfonylspiro(3H-indole-3,4'-piperidin)-1-yl]-2-(benzylamino)-3-[N-(3,4-dichlorobenzyl) benzyloxycarbonyl-amino]pronionamide Benzaldehyde (171 mg) was added to a solution of the product of step (d) (1.17 g) in dichloromethane (50 ml) stirring over MgSO₄. After 18 hours the solution was filtered and the solvent was evaporated under reduced pressure. The residue was dissolved in methanol (20 ml) and treated with sodium borohydride (68 mg). After 2 hours the solvent was evaporated under reduced pressure and the residue was partitioned between ethyl acetate and water. The organic layer was dried (MgSO₄) and the solvent was evaporated under reduced pressure. The residue was purified by MPLC [CH₂Cl₂/MeOH/NH₃(Aq.), 96:3:1] to give the title compound as a colourless solid (410 mg). m/e (CI⁺) 734 (MH⁺).

f) N-[1-Methanesulfonylspiro(3H-indole-3,4'-piperidin)-1-yl]-2-(benzylamino)-3-(3,4-dichlorobenzylamino) propionamide, dihydrochloride Boron tribromide (51.4 mg) was added to a stirred solution of the product of step (e) (190 mg) in dichloromethane at −5° C. After 20 minutes aqueous sodium hydroxide (4M) was added and the mixture was extracted with ethyl acetate (4×20 ml). The combined organic fractions were dried (MgSO₄) and the solvent was evaporated under reduced pressure. The residue was purified by MPLC [CH₂Cl₂/MeOH/NH₃(Aq.), 96:3:1]. The residue was dissolved in ethanolic hydrogen chloride (5M) and the solvent was evaporated under reduced pressure. The residue was triturated with isopropanol and the solid was collected and dried in vacuo to give the title compound as a colourless solid (37 mg). NMR δ$_H$ (250 MHz, DMSO-d₆) 1.63–1.80 (4H, m), 2.09 ( 3H, m), 2.46–2.70 (3H, m), 2.84 (3H, s), 3.46–3.83 (5H, s) 4.56 (1H, m), 6.87–7.34 (12H, m). m/e (CI⁺) 601 (MH⁺).

EXAMPLE 73

N-[1-Methanesulfonylspiro(3H-indole-3,4'-piperidin)-1-yl]-2-(benzylamino)-3-(N-methyl-3,4-dichlorobenzylamino)propionamide, dihydrochloride a) Methyl 2-(tert-butoxycarbonylamino)-3-(N-methyl-3,4-dichlorobenzylamino)propionate Sodium cyanoborohydride (121 mg) was added to a solution of formaldehyde (570 mg), methyl 2-(tert-butoxycarbonylamino)-3-(3,4-dichlorobenzylamino) propionate (720 mg) and acetic acid (0.1 ml) in acetonitrile and the mixture was stirred at room temperature for 30 minutes. Aqueous sodium hydrogen carbonate (10 ml) was added and the mixture was extracted with ethyl acetate (3×20 ml). The combined organic fractions were dried (MgSO₄) and the solvent was evaporated under reduced pressure to give the title compound as a colourless oil (722 mg). NMR δ$_H$ (360 MHz, CDCl₃) 1.45 (9H, s), 2.21 (3H, s), 2.73 (2H, d, J=7.0 Hz), 3.46 (2H, m), 3.75 (3H, s) 4.37 (1H, m), 5.19 (1H, br s), 7.10 (1H, dd, J=11.0 and 1.0 Hz), 7.36 (2H, m).

b) 2-(tert-Butoxycarbonylamino)-3-(N-methyl-3,4-dichlorobenzylamino)propionic acid Lithium hydroxide (55 mg) was added to a solution of the product of step (a) (722 mg) in tetrahydrofuran/water (30 ml). The mixture was stirred at room temperature for 4 hours, diluted with hydrochloric acid (1M, 50 ml) and extracted with ethyl acetate (3×50 ml). The combined organic fractions were dried (MgSO₄) and the solvent was evaporated under reduced pressure to give the title compound as a colourless foam (301 mg). NMR δ$_H$ (250 MHz, CDCl₃) 1.43 (9H, s), 2.59 (3H, s), 2.90 (1H, m), 3.22 (1H, m), 3.77 (1H, m) 4.10 (1H, m), 4.26 (1H, m),5.67 (1H, br s) 7.24 (1H, dd, J=11.0 and 1.0 Hz), 7.68 (2H,m). m/e (CI⁺) 377 (MH⁺).

c) N-[1-Methanesulfonylspiro(3H-indole-3,4'-piperidin)-1-yl]-2-amino -3-[N-methyl-3,4-dichlorobenzylamino] propionamide Bis(2-oxo-3-oxazolidinyl)phosphinic chloride (305 mg) was added to stirred solution of the product of step (b) (301 mg), N-1-methanesulfonylspiro(3H-indole)-3,4'-piperidine (230 mg) and triethylamine (0.36 ml) in dichloromethane (50 ml). The mixture was stirred at room temperature for 18 hours and the solvent was evaporated under reduced pressure. The residue was partitioned between ethyl acetate and water and the organic layer was dried (MgSO₄) and the solvent was evaporated under reduced pressure. The residue was dissolved in dichloromethane (20 ml) and trifluoroacetic acid (2.0 ml) was added. After 2 hours the solvent was evaporated under reduced pressure and the residue was partitioned between aqueous sodium carbonate (saturated, 20 ml) and ethyl acetate (20 ml). The organic layer was dried (MgSO$_4$) and the solvent was evaporated under reduced pressure to give the title compound as a colourless foam. (380 mg). m/e (CI$^+$) 525 (MH$^+$).

d) N-[1-Methanesulfonylspiro(3H-indole-3,4'-piperidin)-1-yl]-2-(benzylamino)-3-(N-methyl-3,4-dichlorobenzylamino)propionamide dihydrochloride Benzaldehyde (80 mg) was added to a solution of the product of step (c) (380 mg) in dichloromethane (50 ml) stirring over MgSO$_4$. After 18 hours the solution was filtered and the solvent was evaporated under reduced pressure. The residue was dissolved in methanol (20 ml) and treated with sodium borohydride (29 mg). After 2 hours the solvent was evaporated under reduced pressure and the residue was partitioned between ethyl acetate and water. The organic layer was dried (MgSO$_4$) and the solvent was evaporated under reduced pressure. The residue was purified by MPLC [CH$_2$Cl$_2$/MeOH/NH$_3$(Aq.), 96:3:1]. The residue was dissolved in ethanolic hydrogen chloride (5M) and the solvent was evaporated under reduced pressure. The residue was triturated with isopropanol and the solid was collected and dried in vacuo to give the title compound as a colourless solid (220 mg). NMR $\delta_H$ (360 MHz, DMSO-d6) 1.60–2.09 ( 7H, m), 2.50–2.72 (3H, m), 2.91 (3H, s), 2.93 (3H, s) 3.46–3.38 (5H, 5) 4.47 (1H, m), 6.87–7.34 (12H, m). m/e (CI$^+$) 615 (MH$^+$).

EXAMPLE 74

N-[1-Methanesulfonylspiro(3H-indole-3,4'-piperidin)-1-yl]-2-(benzylamino)-5-phenylpentanamide, hydrochloride a) 2-[N-(Benzyl)benzyloxycarbonyl]amino-5-phenylpentanoic acid N-Benzyl-N-(benzyloxycarbonyl)serine-β-lactone [prepared according to Vederas, J. C., et. al., *J. Am. Chem. Soc.,* 109, 4649 (1987), 933 mg, 3 mmol] in THF (10 ml) was added dropwise to a stirred, cooled (−78° C.) solution of phenylethyl magnesium bromide dimethyl sulfide complex [prepared from phenylethyl bromide (1.85 g, 10 mmol), magnesium (0.24 g, 10 mmol), copper (I) bromide dimethylsulfide complex (50 mg) and dimethylsulfide (0.5 ml) in THF (20 ml) (Vederas, J. C., et. al., *J. Am. Chem. Soc.,* 109, 4649 (1987)]. The mixture was stirred at −78° C. for 30 minutes then at −23° C. for 2 hours. Aqueous hydrochloric acid (0.1M, 20 ml) was added and the mixture was extracted with ethyl acetate (3×25 ml). The combined organic fractions were dried (MgSO$_4$) and the solvent was evaporated under reduced pressure. The residue was purified by column chromatography on silica gel, eluting with ethyl acetate/ acetic acid (99.9:0.1) to give the title compound (253 mg). NMR $\delta_H$ (250 MHz, CDCl$_3$) 9.6–9.2 (1H, br s), 7.78–7.35 (15H, m), 5.53 (2H, s), 5.31–4.61 (3H, m), 2.78–2.62 (2H, m), and 2.47–1.63 (4H, m).

b) N-[1-Methanesulfonylspiro(3H-indole-3,4'-piperidin)-1-yl]-2-[N-(benzylbenzyloxycarbonyl]amino-5-phenylpentanamide The product of step (a) (250 mg, 0.6 mmol) was dissolved in dichloromethane (5 ml) and 1-methanesulfonylspiro(3H-indole-3,4'-piperidine) hydrochloride (302 mg, 1 mmol), bis(2-oxo-3-oxazolidinyl)phosphinic chloride (254 mg, 2 mmol) and triethylamine (202 mg, 2 mmol) were added. The mixture was stirred at room temperature for 16 hours and the solvent was evaporated under reduced pressure. The residue was dissolved in ethyl acetate, washed with aqueous potassium carbonate (saturated), dried (MgSO$_4$) and the solvent was evaporated under reduced pressure. The residue was purified by column chromatography on silica gel, eluting with ethyl acetate/hexane to give the title compound (160 mg). m/e (CI$^+$) 666 (MH$^+$).

c) N-[1-Methanesulfonylspiro(3H-indole-3,4'-piperidin)-1-yl]-2-(benzylamino)-5phenylpentanamide, hydrochloride Boron tribromide (1M solution in dichloromethane, 1 ml) was added to a stirred cooled (0° C.) solution of the product of step (b) (150 mg, 0.23 mmol) in dichloromethane (1 ml) and the mixture was stirred at 0° C. for 30 minutes. Aqueous sodium hydroxide (2M) was added and the organic layer was washed with water, dried (MgSO$_4$) and the solvent was evaporated under reduced pressure. The residue was purified by column chromatography on silica gel, eluting with dichloromethane/methanol and the residue was treated with methanolic hydrogen chloride. The solvent was evaporated under reduced pressure and the residue was freeze dried to give the title compound as an amorphous solid (165 mg). Found: C, 65.78; H, 6.94; N, 7.65. C$_{31}$H$_{37}$N$_3$O$_3$S.HCl requires: C, 65.53; H, 6.75; N, 7.40%. m/e (CI$^+$) 532 (MH$^+$).

EXAMPLE 75

N-[1-Methanesulfonylspiro(3H-indole-3,4'-piperidin)-1-yl]-2-(benzylamino)-5-(3,4-dichlorophenyl)pentanamide, hydrochloride a) Ethyl 5-(3,4-dichlorophenyl-2-oxopentanoate 3-(3,4-Dichlorophenyl)propylmagnesium bromide [prepared from 3-(3,4-dichlorophenyl)propyl bromide (2.7 g, 10 mmol) and magnesium (0.24 g, 10 mmol) in ether (*Ger. Offen.* DE1965711)] was added dropwise to a stirred, cooled (−10° C.) solution of diethyl oxalate (1.75 g, 4.2 mmol) in ether (60 ml). THF (15 ml) was added and the mixture was stirred at room temperature for 0.5 hours. Hydrochloric acid (2M) was added and the organic layer was diluted with hexane, washed with brine and aqueous sodium hydrogen carbonate (saturated), dried (MgSO$_4$) and the solvent was evaporated under reduced pressure. The residue was purified by column chromatography on silica gel, eluting with ethyl acetate/hexane (25:75) to give the title compound as an oil (0.7 g). NMR $\delta_H$ (360 MHz, CDCl$_3$) 7.35 (1H, d, J=6.4 Hz), 7.28 (1H, d, J=2 Hz), 7.01 (1H, dd, J=6.4, 2 Hz), 4.39–4.25 (2H, m), 2.84 (2H, t, J=7.2 Hz), 2.62 (2H, t, J=7.2 Hz), 2.09–1.91 (2H, pent, J=8 Hz), and 1.33 (3H, t, J=7 Hz).

b) Ethyl 2-(Benzylamino)-5-(3,4-dichlorophenyl) pentanoate

Acetic acid (0.42 g, 7 mmol) was added to a mixture of the product of step (a) (1.0 g, 3.5 mmol), benzylamine (0.75 g, 7 mmol) and sodium cyanoborohydride (440 mg, 7 mmol) in ethanol (10 ml) and the mixture was stirred at room temperature for 72 hours. The solvent was evaporated under reduced pressure and the residue was partitioned between ethyl acetate and aqueous potassium carbonate (saturated). The organic layer was dried (MgSO$_4$) and the solvent was evaporated under reduced pressure. The residue was purified by column chromatography on silica gel, eluting with ethyl acetate/hexane (5:95) to give the title compound (400 mg). NMR $\delta_H$ (360 MHz, CDCl$_3$) 7.32–7.23 (7H, m), 6.96 (1H, dd, J=8.4, 2.2 Hz), 4.18 (2H, q, J=7 Hz), 3.81 (1H, d, J=12.9 Hz), 3.61 (1H, d, J=12.9 Hz), 3.23 (1H, t, J=7.2 Hz), 2.54 (2H, m), 1.69–1.60 (4H, m), and 1.28 (3H, t, J=7 Hz).

c) Ethyl 2-[N-(benzyl)-tert-butyloxycarbonylamino]-5-(3,4-dichlorophenyl)pentanoate Di-tert-butyldicarbonate (400 mg) was added to the product of step (b) (400 mg) in dichloromethane (10 ml) and the mixture was stirred at room temperature for 72 hours. The solvent was evaporated under reduced pressure and the residue was purified by column chromatography on silica gel, eluting with hexane/ethyl acetate (100:0 increasing to 95:5) to give the title compound (350 mg). NMR δ$_H$ (360 MHz, CDCl) 7.29–7.11 (6H, m), 7.12–7.11 (1H, m), 6.87–6.85 (1H, m), 4.11–3.88 (5H, m), 2.44–1.29 (6H, m), 1.42 (9H, s), and 1.20 (3H, t, J=7 Hz).

d) N-[1 -Methanesulfonylspiro(3H-indole-3,4'-piperidin)-1-yl]-2-(benzylamino)-5-(3,4-dichlorophenyl)pentanamide, hydrochloride A solution of lithium hydroxide (100 mg) in water (10 ml) was added to a solution of the product of step (c) (350 mg) in THF (10 ml) and the mixture was stirred at room temperature for 16 hours. The mixture was acidified with aqueous citric acid (10%) and extracted with ethyl acetate (3×25 ml). The combined organic fractions were dried (MgSO$_4$) and the solvent was evaporated under reduced pressure. The residue was dissolved in dichloromethane (5 ml) and 1-methanesulfonylspiro(3H-indole-3,4'-piperidine) hydrochloride (215 mg, 0.71 mmol), bis(2-oxo-3-oxazolidinyl)phosphinic chloride (199 mg, 0.78 mmol) and triethylamine (202 mg, 2 mmol) were added. The mixture was stirred at room temperature for 16 hours and the solvent was evaporated under reduced pressure. The residue was dissolved in ethyl acetate, washed with aqueous potassium carbonate (saturated), dried (MgSO$_4$) and the solvent was evaporated under reduced pressure. The residue was purified by column chromatography on silica gel, eluting with ethyl acetate/hexane and the residue was dissolved in ethanolic hydrogen chloride (5M). The solvent was evaporated under reduced pressure and the residue was freeze dried to give the title compound as an amorphous solid (235 mg). Found: C, 58.66; H, 5.70; N, 6.60. C$_{31}$H$_{35}$Cl$_2$N$_3$O$_3$S.HCl requires: C, 58.45; H, 5.70; N, 6.60%. m/e (CI$^+$) 600 (MH$^+$).

EXAMPLE 76

N-[1-Methanesulfonylspiro(3H-indole-3,4'-piperidin)-1-yl]-2-(benzylamino)-5-(3,4-dichlorophenyl)butanamide, hydrochloride a) Ethyl 4-(3,4-Dichlorophenyl)-2-oxobutanoate 2-(3,4-Dichlorophenyl)ethyl bromide (5 g, 19.7 mmol) was added slowly to a suspension of magnesium turnings (0.48 g, 19.7 mmol) in ether (30 ml). After spontaneous reflux had finished the mixture was stirred under reflux for 15 minutes and allowed to cool to room temperature. The mixture was added dropwise via cannula to a stirred, cooled (−25° C.) solution of diethyl oxalate (3 g, 20.7 mmol) in THF (15 ml). The mixture was stirred at −10° C. for 30 minutes and allowed to warm to room temperature. Hydrochloric acid (2M, 15 ml) was added and the mixture was extracted with ether (2×20 ml). The combined organic fractions were washed with water, dried (Na$_2$SO$_4$) and the solvent was evaporated under reduced pressure. The residue was purified by column chromatography on silica gel, eluting with ethyl acetate/hexane (10:90) to give the title compound (0.7 g).

b) Ethyl 2-(benzylamino)-4-(3,4-dichlorophenyl)butanoate

A mixture of acetic acid (0.29 ml, 5 mmol), the product of step (a) (700 mg, 2.5 mmol), benzylamine (0.56 ml, 5 mmol) and sodium cyanoborohydride (320 mg, 5 mmol) in ethanol (10 ml) was stirred at room temperature for 16 hours. The solvent was evaporated under reduced pressure and the residue was partitioned between ethyl acetate and aqueous sodium carbonate (saturated). The organic layer was dried (Na$_2$SO$_4$) and the solvent was evaporated under reduced pressure. The residue was purified by column chromatography on silica gel, eluting with ethyl acetate/hexane (10:90) to give the title compound as an oil (310 mg). m/e (CI$^+$) 366 (MH$^+$).

c) Ethyl 2-[N-(benzyl)-tert-butyloxycarbonylamino]-4-(3,4-dichlorophenyl)butanoate Di-tert-butyldicarbonate (900 mg, 4.1 mmol) was added to the product of step (b) (300 mg, 0.82 mmol) in dichloromethane (10 ml) and the mixture was stirred at room temperature for 5 days. The solvent was evaporated under reduced pressure and the residue was purified by column chromatography on silica gel, eluting with hexane/ethyl acetate (90:10) to give the title compound as an oil (281 mg). m/e (CI$^+$) 466 (MH$^+$).

d) 2-[N-(Benzyl)-tert-butyloxycarbonylamino]-4-(3,4-dichlorophenyl)butanoic acid Lithium hydroxide (80 mg 1.8 mmol) and water (2 ml) were added to a solution of the product of step (c) (280 mg, 0.6 mmol) in THF (5 ml) and the mixture was stirred at room temperature for 16 hours. Acetic acid (0.5 ml) was added and the mixture was partitioned between ethyl acetate and water. The organic layer was dried (Na$_2$SO$_4$) and the solvent was evaporated under reduced pressure to give the title compound as a colourless foam (234 mg) m/e (CI$^+$) 438 (MH$^+$).

e) N-[1-Methanesulfonylspiro(3H-indole-3,4'-piperidin)-1-yl]-2-(benzylamino)-4-(3,4-dichlorophenyl)butanamide, hydrochloride A mixture of the product of step (e) (230 mg, 0.53 mmol), 1-methanesulfonylspiro(3H-indole-3,4'-piperidine) hydrochloride (159 mg, 0.53 mmol), bis(2-oxo-3-oxazolidinyl) phosphinic chloride (160 mg, 0.64 mmol) and triethylamine (0.18 ml, 1.33 mmol) in dichloromethane (10 ml) was stirred at room temperature for 16 hours. Dichloromethane (10 ml) was added and the mixture was washed with aqueous sodium carbonate (saturated) and aqueous citric acid (10%), dried (Na$_2$SO$_4$) and the solvent was evaporated under reduced pressure. The residue was purified by column chromatography on silica gel, eluting with ethyl acetate/hexane (70:30). The residue was dissolved in methanol (2 ml) and methanolic hydrogen chloride (5 ml) was added. The mixture was stirred at room temperature for 16 hours and the solvent was evaporated under reduced pressure. The residue was dissolved in methanol (2 ml) and ether was added. The solid was collected and dried in vacuo to give the title compound as a colourlesss solid (235 mg). Found: C, 57.36; H, 5.53; N, 6.71. C$_{30}$H$_{33}$Cl$_2$N$_3$O$_3$S.HCl.0.25H$_2$O requires: C, 57.42; H, 5.54; N, 6.70%. m/e (CI$^+$) 586 (NM$^+$).

We claim:

1. A compound of formula (I):

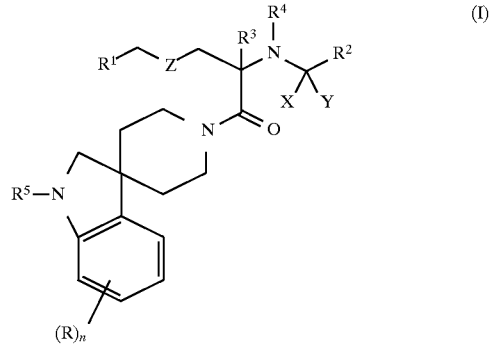

wherein n is zero, 1, 2 or 3;

R represents C$_{1-6}$alkyl, C$_{1-6}$alkoxy, hydroxy, halogen, cyano, trifluoromethyl, SO$_2$C$_{1-6}$alkyl, NR$^a$R$^b$, NR$^a$COR$^b$, or CONR$^a$R$^b$, where R$^a$ and R$^b$ each independently represent hydrogen, C$_{1-6}$alkyl, phenyl or trifluoromethyl;

R$^1$ represents unsubstituted phenyl or phenyl substituted by 1, 2 or 3 groups selected from C$_{1-6}$alkyl, C$_{2-6}$alkenyl, C$_{2-6}$alkynyl, C$_{3-7}$cycloalkyl, $C_{3-7}$cycloalkyl$C^{1-4}$alkyl, —O(CH$_2$)$_p$O— where p is 1 or 2, halogen, cyano, nitro, trifluoromethyl, trimethylsilyl, OR$^a$, SR$^a$, SOR$^a$, SO$_2$R$^a$, NR$^a$R$^b$, NR$^a$COR$^b$, NR$^a$CO$_2$R$^b$, COR$^a$, CO$_2$R$^a$ or CONR$^a$R$^b$, where R$^a$ and R$^b$ are as previously defined; naphthyl; benzhydryl; or benzyl, where the naphthyl group or each phenyl moiety of benzyl and benzhydryl may be substituted by $C_{1-6}$alkyl, $C_{1-6}$alkoxy, halogen or trifluoromethyl;

R$^2$ represents hydrogen; unsubstituted phenyl or phenyl substituted by 1, 2 or 3 groups selected from $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, —O(CH$_2$)$_p$O— where p is 1 or 2, halogen, cyano, nitro, trifluoromethyl, trimethylsilyl, OR$^a$, SR$^a$, SOR$^a$, SO$_2$R$^a$, NR$^a$R$^b$, NR$^a$COR$^b$, NR$^a$CO$_2$R$^b$, COR$^a$, CO$_2$R$^a$ or CONR$^a$R$^b$, where R$^a$ and R$^b$ are as previously defined; heteroaryl selected from indazolyl, thienyl, furanyl, pyridyl, thiazolyl, tetrazolyl and quinolinyl; naphthyl; benzhydryl; or benzyl; wherein each heteroaryl, the naphthyl group and each phenyl moiety of benzyl and benzhydryl may be substituted by $C_{1-6}$alkyl, $C_{1-6}$alkoxy, halogen or trifluoromethyl;

R$^3$ and R$^4$ each independently represents hydrogen or $C_{1-6}$alkyl or R$^3$ and R$^4$ together are linked so as to form a $C_{1-3}$alkylene chain;

R$^5$ represents hydrogen, $C_{1-6}$alkyl, $C_{3-7}$cycloalkyl, $C_{3-7}$cycloalkyl$C_{1-4}$alkyl, phenyl$C_{1-4}$alkyl, CO$_2$R$^a$, CONR$^a$R$^b$, SOR$^a$ or SO$_2$R$^a$, wherein the phenyl moiety may be substituted by $C_{1-6}$alkyl, $C_{1-6}$alkoxy, halogen or trifluoromethyl, and R$^a$ and R$^b$ are as previously defined;

X and Y each independently represents hydrogen, or together form a group =O; and Z represents a bond, O, S, SO, SO$_2$, NR$^6$, or —(CR$^6$R$^6$)— where each R$^6$ is hydrogen or $C_{1-6}$alkyl;

or a pharmaceutically acceptable salt thereof.

2. A compound as claimed in claim 1 wherein
n is zero, 1, 2 or 3;

R represents $C_{1-6}$alkyl, $C_{1-6}$alkoxy, hydroxy, halogen, cyano, trifluoromethyl, SO$_2$$C_{1-6}$alkyl, NR$^a$R$^b$, NR$^a$COR$^b$, or CONR$^a$R$^b$, where R$^a$ and R$^b$ each independently represent hydrogen, $C_{1-6}$alkyl, phenyl or trifluoromethyl;

R$^1$ represents phenyl optionally substituted by 1, 2 or 3 groups selected from $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, —O(CH$_2$)$_p$O— where p is 1 or 2, halogen, cyano, nitro, trifluoromethyl, trimethylsilyl, OR$^a$, SR$^a$, SOR$^a$, SO$_2$R$^a$, NR$^a$R$^b$, NR$^a$COR$^b$, NR$^a$CO$_2$R$^b$, COR$^a$, CO$_2$R$^a$ or CONR$^a$R$^b$, where R$^a$ and R$^b$ are as previously defined;

R$_2$ represents phenyl optionally substituted by 1, 2 or 3 groups selected from $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, —O(CH$_2$)$_p$O— where p is 1 or 2, halogen, cyano, nitro, trifluoromethyl, trimethylsilyl, OR$^a$, SR$^a$, SOR$^a$, SO$_2$R$^a$, NR$^a$R$^b$, NR$^a$COR$^b$, NR$^a$CO$_2$R$^b$, COR$^a$, CO$_2$R$^a$ or CONR$^a$R$^b$, where R$^a$ and R$^b$ are as previously defined; heteroaryl selected from indazolyl, thienyl, furanyl, pyridyl, thiazolyl, tetrazolyl and quinolinyl; naphthyl; benzhydryl; or benzyl; wherein each heteroaryl, the naphthyl group and each phenyl moiety of benzyl and benzhydryl may be substituted by $C_{1-6}$alkyl, $C_{1-6}$alkoxy, halogen or trifluoromethyl;

R$^3$ and R$^4$ each independently represents hydrogen or $C_{1-6}$alkyl;

R$^5$ represents hydrogen, $C_{1-6}$alkyl, $C_{3-7}$cycloalkyl, $C_{3-7}$cycloalkyl$C_{1-4}$alkyl, phenyl$C_{1-4}$alkyl, CO$_2$R$^a$, CONR$^a$R$^b$, SOR$^a$ or SO$_2$R$^a$, wherein the phenyl moiety may be substituted by $C_{1-6}$alkyl, $C_{1-6}$alkoxy, halogen or trifluoromethyl, and R$^a$ and R$^b$ are as previously defined;

X and Y each independently represents hydrogen, or together form a group =O; and Z represents O, S, or NR$^6$, where R$^6$ is hydrogen or $C_{1-6}$alkyl;

or a pharmaceutically acceptable salt thereof.

3. A compound as claimed in claim 1 of the formula (Ia):

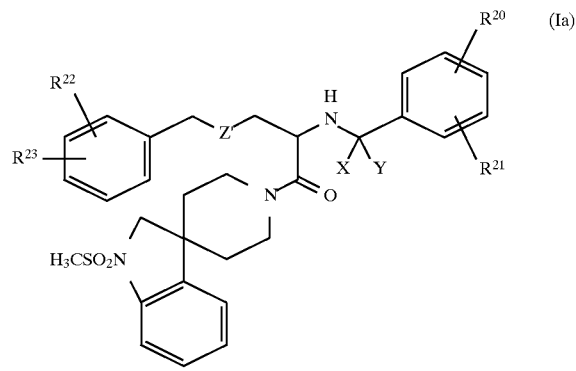

wherein
X and Y are as defined in claim 1;
Z' is O, S or —CH$_2$—;
R$^{20}$ and R$^{21}$ independently represent hydrogen, $C_{1-6}$alkyl, halogen, trifluoromethyl, OR$^a$, or NR$^a$R$^b$, where R$^a$ and R$^b$ are as defined in claim 1; and
R$^{22}$ and R$^{23}$ independently represent hydrogen or halogen;
or a pharmaceutically acceptable salt thereof.

4. A compound as claimed in claim 1 of the formula (Ib):

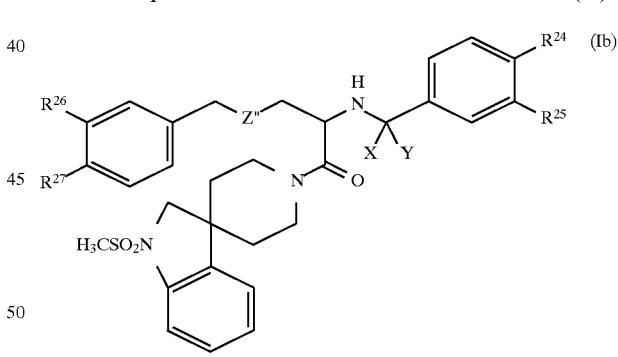

wherein
Z'' is O or —CH$_2$—;
R$^{24}$ and R$^{25}$ independently represent hydrogen or chlorine; and
R$^{26}$ and R$^{27}$ independently represent hydrogen or chlorine, with the proviso that at least one of R$^{26}$ and R$^{27}$ represents chlorine;
or a pharmaceutically acceptable salt thereof.

5. A compound as claimed in claim 1 wherein n is zero.

6. A compound as claimed in claim 1 wherein R$^1$ represents unsubstituted phenyl or phenyl substituted by one or two groups selected from $C_{1-6}$alkyl, halogen and trifluoromethyl.

7. A claim as claimed in claim 6 wherein R$^1$ represents disubstituted phenyl.

8. A compound as claimed in claim 1 wherein $R^2$ represents unsubstituted or substituted phenyl, thienyl, furanyl, pyridyl, quinolinyl, naphthyl, or benzhydryl.

9. A compound as claimed in claim 8 wherein $R^2$ represents unsubstituted phenyl or phenyl substituted by one or two groups selected from chlorine, fluorine, methyl, trifluoromethyl, methoxy and dimethylamino.

10. A compound as claimed in claim 1 wherein $R^3$ and $R^4$ each independently represent hydrogen.

11. A compound as claimed in claim 1 wherein $R^5$ represents the group $SO_2R^a$ where $R^a$ is as defined in claim 1.

12. A compound as claimed in claim 11 wherein $R^5$ represents $SO_2CH_3$.

13. A compound as claimed in claim 1 wherein Z is an oxygen atom.

14. A compound as claimed in claim 1 wherein Z is —$CH_2$—.

15. A compound selected from:
N-[1-methanesulphonylspiro(3H-indole-3,4'-piperidin)-1-yl]-3-benzyloxy-2-(3,4-dichlorobenzamido)propionamide;
N-[1-methanesulphonylspiro(3H-indole-3,4'-piperidin)-1-yl]-3-benzyloxy-2-(3-pyridylcarboxamido)propionamide;
N-[1-methanesulphonylspiro(3H-indole-3,4'-piperidin)-1-yl]-3-benzyloxy-2-(2-chlorobenzamido)propionamide;
N-[1-methanesulphonylspiro(3H-indole-3,4'-piperidin)-1-yl]-3-benzyloxy-2-(3-chlorobenzamido)propionamide;
N-[1-methanesulphonylspiro(3H-indole-3,4'-piperidin)-1-yl]-3-benzyloxy-2-(4-chlorobenzamido)propionamide;
N-[1-methanesulphonylspiro(3H-indole-3,4'-piperidin)-1-yl]-3-benzyloxy-2-(2,6-dichlorobenzamido)propionamide;
N-[1-methanesulphonylspiro(3H-indole-3,4'-piperidin)-1-yl]-3-benzyloxy-2-(3,5-dichlorobenzamido)propionamide;
N-[1-methanesulphonylspiro(3H-indole-3,4'-piperidin)-1-yl]-3-benzyloxy-2-(2,5-dichlorobenzamido)propionamide;
N-[1-methanesulphonylspiro(3H-indole-3,4'-piperidin)-1-yl]-3-benzyloxy-2-(2,4-dichlorobenzamido)propionamide;
N-[1-methanesulphonylspiro(3H-indole-3,4'-piperidin)-1-yl]-3-benzyloxy-2-(2,3-dichlorobenzamido)propionamide;
N-[1-methanesulphonylspiro(3H-indole-3,4'-piperidin)-1-yl]-3-benzyloxy-2-(3,4-dimethoxybenzamido)propionamide;
N-[1-methanesulphonylspiro(3H-indole-3,4'-piperidin)-1-yl]-3-benzyloxy-2-benzamidopropionamide;
N-[1-methanesulphonylspiro(3H-indole-3,4'-piperidin)-1-yl]-3-benzyloxy-2-(3-(2-propyloxy)benzamido)propionamide;
N-[1-methanesulphonylspiro(3H-indole-3,4'-piperidin)-1-yl]-3-benzyloxy-2-[(1-naphthyl)carboxamido)]propionamide;
N-[1-methanesulphonylspiro(3H-indole-3,4'-piperidin)-1-yl]-3-benzyloxy-2-[(2-naphthyl)carboxamido)]propionamide;
N-[1-methanesulphonylspiro(3H-indole-3,4'-piperidin)-1-yl]-3-benzyloxy-2-(phenylacetamido)propionamide;
N-[1-methanesulphonylspiro(3H-indole-3,4'-piperidin)-1-yl]-3-benzyloxy-2-(3,4-dichlorophenylacetamido)propionamide;
N-[1-methanesulphonylspiro(3H-indole-3,4'-piperidin)-1-yl]-3-benzyloxy-2-[(3,5-bis(trifluoromethyl)phenyl)acetamido]propionamide;
N-[1-methanesulphonylspiro(3H-indole-3,4'-piperidin)-1-yl]-3-benzyloxy-2-(diphenylacetamido)propionamide;
N-[1-methanesulphonylspiro(3H-indole-3,4'-piperidin)-1-yl]-3-benzyloxy-2-(4-pyridylcarboxamido)propionamide;
N-[1-methanesulphonylspiro(3H-indole-3,4'-piperidin)-1-yl]-3-benzyloxy-2-(2-pyridylcarboxamido)propionamide;
N-[1-methanesulphonylspiro(3H-indole-3,4'-piperidin)-1-yl]-3-benzyloxy-2-(8-quinolinylcarboxamido)propionamide;
or a pharmaceutically acceptable salt thereof.

16. A compound selected from:
N-[1-methanesulphonylspiro(3H-indole-3,4'-piperidin)-1-yl]-3-benzyloxy-2-(3,4-dichlorobenzylamino)propionamide;
N-[1-methanesulphonylspiro(3H-indole-3,4'-piperidin)-1-yl]-3-benzyloxy-2-(2-methylbenzylamine)propionamide;
N-[1-methanesulphonylspiro(3H-indole-3,4'-piperidin)-1-yl]-2-benzylamino-3-benzyloxypropionamide;
N-[1-methanesulphonylspiro(3H-indole-3,4'-piperidin)-1-yl]-3-benzyloxy-2-(2-chlorobenzylamino)propionamide;
N-[1-methanesulphonylspiro(3H-indole-3,4'-piperidin)-1-yl]-3-benzyloxy-2-(3-chlorobenzylamino)propionamide;
N-[1-methanesulphonylspiro(3H-indole-3,4'-piperidin)-1-yl]-3-benzyloxy-2-(4-chlorobenzylamino)propionamide;
N-[1-methanesulphonylspiro(3H-indole-3,4'-piperidin)-1-yl]-3-benzyloxy-2-(3-bromobenzylamino)propionamide;
N-[1-methanesulphonylspiro(3H-indole-3,4'-piperidin)-1-yl]-3-benzyloxy-2-(3-fluorobenzylamino)propionamide;
N-[1-methanesulphonylspiro(3H-indole-3,4'-piperidin)-1-yl]-3-benzyloxy-2-(3-cyanobenzylamino)propionamide;
N-[1-methanesulphonylspiro(3H-indole-3,4'-piperidin)-1-yl]-3-benzyloxy-2-(3-nitrobenzylamino)propionamide;
N-[1-methanesulphonylspiro(3H-indole-3,4'-piperidin)-1-yl]-3-benzyloxy-2-(3-methylbenzylamino)propionamide;
N-[1-methanesulphonylspiro(3H-indole-3,4'-piperidin)-1-yl]-3-benzyloxy-2-(3-methoxybenzylamino)propionamide;
N-[1-methanesulphonylspiro(3H-indole-3,4'-piperidin)-1-yl]-3-benzyloxy-2-(4-methoxybenzylamino)propionamide;
N-[1-methanesulphonylspiro(3H-indole-3,4'-piperidin)-1-yl]-3-benzyloxy-2-(4-(dimethylamino)benzylamino)propionamide;
N-[1-methanesulphonylspiro(3H-indole-3,4'-piperidin)-1-yl]-3-benzyloxy-2-(2,4-dichlorobenzylamino)propionamide;
N-[1-methanesulphonylspiro(3H-indole-3,4'-piperidin)-1-yl]-3-benzyloxy-2-(3,5-dichlorobenzylamino)propionamide;
N-[1-methanesulphonylspiro(3H-indole-3,4'-piperidin)-1-yl]-3-benzyloxy-2-(2,3-dichlorobenzylamino)propionamide;
N-[1-methanesulphonylspiro(3H-indole-3,4'-piperidin)-1-yl]-3-benzyloxy-2-(2,6-dichlorobenzylamino)propionamide;
N-[1-methanesulphonylspiro(3H-indole-3,4'-piperidin)-1-yl]-3-benzyloxy-2-(3,5-dimethoxybenzylamino)propionamide;
N-[1-methanesulphonylspiro(3H-indole-3,4'-piperidin)-1-yl]-3-benzyloxy-2-(3-chloro-5-methoxybenzylamino)propionamide;
N-[1-methanesulphonylspiro(3H-indole-3,4'-piperidin)-1-yl]-3-benzyloxy-2-(3,4-dimethoxybenzylamino)propionamide;
N-[1-methanesulphonylspiro(3H-indole-3,4'-piperidin)-1-yl]-3-benzyloxy-2-(3,4-methylenedioxybenzylamino)propionamide;

N-[1-methanesulphonylspiro(3H-indole-3,4'-piperidin)-1-yl]-3-benzyloxy-2-(1-naphthylmethylamino)propionamide;
N-[1-methanesulphonylspiro(3H-indole-3,4'-piperidin)-1-yl]-3-benzyloxy-2-(2-naphthylmethylamino)propionamide;
N-[1-methanesulphonylspiro(3H-indole-3,4'-piperidin)-1-yl]-3-benzyloxy-2-(2-pyridylmethylamino)propionamide;
N-[1-methanesulphonylspiro(3H-indole-3,4'-piperidin)-1-yl]-3-benzyloxy-2-(3-pyridylmethylamino)propionamide;
N-[1-methanesulphonylspiro(3H-indole-3,4'-piperidin)-1-yl]-3-benzyloxy-2-(4-pyridylmethylamino)propionamide;
N-[1-methanesulphonylspiro(3H-indole-3,4'-piperidin)-1-yl]-3-benzyloxy-2-(2-furylmethylamino)propionamide;
N-[1-methanesulphonylspiro(3H-indole-3,4'-piperidin)-1-yl]-3-benzyloxy-2-[(5-methylfur-2-yl)methylamino]propionamide;
N-[1-methanesulphonylspiro(3H-indole-3,4'-piperidin)-1-yl]-3-benzyloxy-2-[(3-methylthiophen-2-yl)methylamino]propionamide;
N-[1-methanesulphonylspiro(3H-indole-3,4'-piperidin)-1-yl]-3-benzyloxy-2-[(5-methylthiophen-2-yl)methylamino]propionamide;
N-[1-methanesulphonylspiro(3H-indole-3,4'-piperidin)-1-yl]-3-benzyloxy-2-(N-(3,4-dichlorobenzyl)-N-(methyl)amino)propionamide;
N-[1-methanesulphonylspiro(3H-indole-3,4'-piperidin)-1-yl]-2-benzylamino-3-(2-chlorobenzyloxy)propionamide;
N-[1-methanesulphonylspiro(3H-indole-3,4'-piperidin)-1-yl]-2-benzylamino-3-(3-chlorobenzyloxy)propionamide;
N-[1-methanesulphonylspiro(3H-indole-3,4'-piperidin)-1-yl]-2-benzylamino-3-(4-chlorobenzyloxy)propionamide;
N-[1-methanesulphonylspiro(3H-indole-3,4'-piperidin)-1-yl]-3-(2-chlorobenzyloxy)-2-(3,4-dichlorobenzylamino)propionamide;
N-[1-methanesulphonylspiro(3H-indole-3,4'-piperidin)-1-yl]-3-(3-chlorobenzyloxy)-2-(3,4-dichlorobenzylamino)propionamide;
N-[1-methanesulphonylspiro(3H-indole-3,4'-piperidin)-1-yl]-3-(4-chlorobenzyloxy)-2-(3,4-dichlorobenzylamino)propionamide;
N-[1-methanesulphonylspiro(3H-indole-3,4'-piperidin)-1-yl]-3-(benzylthio)-2-(3,4-dichlorobenzylamino)propionamide;
N-[1-methanesulphonylspiro(3H-indole-3,4'-piperidin)-1-yl]-2-benzylamino-3-(3,4-dichlorobenzyloxy)propionamide;
N-[1-methanesulphonylspiro(3H-indole-3,4'-piperidin)-1-yl]-3-(3,4-dichlorobenzyloxy)-2-(3,4-dichlorobenzylamino)propionamide;
or a pharmaceutically acceptable salt thereof.

17. A compound selected from:
N-[1-methanesulfonylspiro(3H-indole-3,4'-piperidin)-1-yl]-2-(benzylamino)-3-[(napth-2-yl)methoxy]propionamide;
N-[1-methanesulfonylspiro(3H-indole-3,4'-piperidin)-1-yl]-2-(benzylamino)-3-[(napth-1-yl)methoxy]propionamide;
N-[1-methanesulfonylspiro(3H-indole-3,4'-piperidin)-1-yl]-2-[N-(methyl)benzylamino]-3-(3,4-dichlorobenzyloxy)propionamide;
N-[1-methanesulfonylspiro(3H-indole-3,4'-piperidin)-1-yl]-3-(3,4-dichlorobenzyloxy)-2-(dimethyl)aminopropionamide;
N-[1-methanesulfonylspiro(3H-indole-3,4'-piperidin)-1-yl]-3-(3,4-dichlorobenzylthio)-2-(benzylamino)propionamide;
N-[1-methanesulfonylspiro(3H-indole-3,4'-piperidin)-1-yl]-3-(3,4-dichlorobenzylsulfonyl)-2-(benzylamino)propionamide;
N-[1-methanesulfonylspiro(3H-indole-3,4'-piperidin)-1-yl]-2,3-bis(benzylamino)propionamide;
N-[1-methanesulfonylspiro(3H-indole-3,4'-piperidin)-1-yl]-2-(benzylamino)-3-(3,4-dichlorobenzylamino)propionamide;
N-[1-methanesulfonylspiro(3H-indole-3,4'-piperidin)-1-yl]-2-(benzylamino)-3-(N-methyl-3,4-dichlorobenzylamino)propionamide;
N-[1-methanesulfonylspiro(3H-indole-3,4'-piperidin)-1-yl]-2-(benzylamino)-5-phenylpentanamide;
N-[1-methanesulfonylspiro(3H-indole-3,4'-piperidin)-1-yl]-2-(benzylamino)-5-(3,4-dichlorophenyl)pentanamide;
N-[1-methanesulfonylspiro(3H-indole-3,4'-piperidin)-1-yl]-2-(benzylamino)-5-(3,4-dichlorophenyl)butanamide;

or a pharmaceutically acceptable salt thereof.

18. A compound selected from:

N-[1-methanesulfonylspiro(3H-indole-3,4'-piperidin)-1-yl]-2-(benzylamino)-3-(3,4-dichlorobenzyloxy)propionamide;
N-[1-methanesulfonylspiro(3H-indole-3,4'-piperidin)-1-yl]-2-(3,4-dichlorobenzylamino)-3-(3,4-dichlorobenzyloxy)propionamide;

or a pharmaceutically acceptable salt thereof.

19. A pharmaceutical composition comprising a compound as claimed in claim 1 in association with a pharmaceutically acceptable carrier or excipient.

20. A method for the treatment of physiological disorders associated with an excess of tachykinins, which method comprises administration to a patient in need thereof of a tachykinin reducing amount of a compound according to claim 1, or a pharmaceutically acceptable salt thereof.

21. A method for the treatment or prevention of pain or inflammation, which method comprises administration to a patient in need thereof a tachykinin reducing amount of a compound according to claim 1, or a pharmaceutical salt thereof.

22. A method for the treatment or prevention of migraine, which method comprises administration to a patient in need thereof a tachykinin reducing amount of a compound according to claim 1, or a pharmaceutical salt thereof.

23. A method for the treatment or prevention of emesis, which method comprises administration to a patient in need thereof a tachykinin reducing amount of a compound according to claim 1, or a pharmaceutical salt thereof.

24. A method according to claim 20 for the treatment of postherpetic neuralgia.

25. A process for the preparation of a compound of claim 1, which comprises:

(A), where X and Y are both hydrogen, reacting a compound of formula (II):

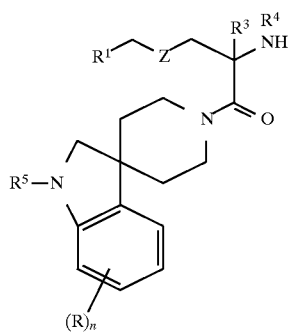
(II)

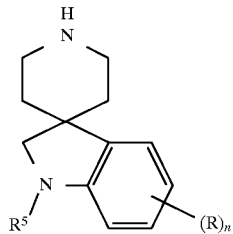
(IV)

wherein R, $R^1$, $R^3$, $R^4$, $R^5$, Z and n are as defined in claim 1, with an aldehyde of formula $R^2$—CHO in the presence of a reducing agent; or (B), where X and Y together form a group =O, may be prepared by the reaction of a compound of formula (II) with an acyl halide of formula $R^2$—COHal where Hal is a halogen atom; or (C) by the reaction of a compound of formula (III) with a piperidinyl derivative of formula (IV):

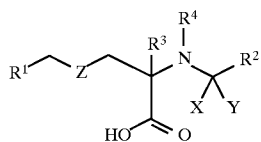
(III)

wherein R, $R^1$, $R^2$, $R^3$, $R^4$, $R^5$, X, Y, Z and n are as defined in claim 1 with the proviso that $R^5$ is not hydrogen;

each process being followed, where necessary, by the removal of any protecting group where present;

and when the compound of formula (I) is obtained as a mixture of enantiomers or diastereoisomers, optionally resolving the mixture to obtain the desired enantiomer;

and/or, if desired, converting the resulting compound of formula (I) or a salt thereof, into a pharmaceutically acceptable salt thereof.

* * * * *